(12) United States Patent
Maase et al.

(10) Patent No.: US 7,351,339 B2
(45) Date of Patent: Apr. 1, 2008

(54) METHOD FOR THE SEPARATION OF ACIDS FROM CHEMICAL REACTION MIXTURES BY MEANS OF IONIC FLUIDS

(75) Inventors: Matthias Maase, Speyer (DE); Klemens Massonne, Bad Duerkheim (DE); Klaus Halbritter, Heidelberg (DE); Ralf Noe, Mannheim (DE); Michael Bartsch, Neustadt (DE); Wolfgang Siegel, Limburgerhof (DE); Veit Stegmann, Mannheim (DE); Miguel Flores, Mannheim (DE); Oliver Huttenloch, Neulussheim (DE); Michael Becker, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 124 days.

(21) Appl. No.: 10/467,065

(22) PCT Filed: Jan. 21, 2003

(86) PCT No.: PCT/EP03/00545

§ 371 (c)(1),
(2), (4) Date: Aug. 19, 2003

(87) PCT Pub. No.: WO03/062171

PCT Pub. Date: Jul. 31, 2003

(65) Prior Publication Data

US 2004/0073035 A1    Apr. 15, 2004

(30) Foreign Application Priority Data

Jan. 24, 2002 (DE) ............... 102 02 838
Jul. 4, 2002 (DE) ............... 102 30 222
Oct. 18, 2002 (DE) ............... 102 48 902
Oct. 31, 2002 (DE) ............... 102 51 140

(51) Int. Cl.
B01D 11/00    (2006.01)
(52) U.S. Cl. ............... 210/638; 210/639; 210/749
(58) Field of Classification Search ............... 210/634, 210/638, 639, 644, 749, 757, 758; 564/12–14, 564/493; 562/8–25; 552/1; 546/187; 549/462
See application file for complete search history.

(56) References Cited

U.S. PATENT DOCUMENTS

| | | | |
|---|---|---|---|
| 3,719,617 A * | 3/1973 | Schobinger et al. ......... 524/30 |
| 3,773,809 A | 11/1973 | Walter | |
| 3,779,907 A * | 12/1973 | Li et al. ............... 210/638 |
| 3,860,656 A * | 1/1975 | McCain et al. ............ 568/492 |
| 3,903,120 A | 9/1975 | Shook, Jr. et al. | |
| 4,014,785 A * | 3/1977 | Li et al. ............... 210/638 |
| 4,029,744 A * | 6/1977 | Li et al. ............... 423/356 |
| 4,536,351 A | 8/1985 | Neumaier | |
| 4,851,550 A | 7/1989 | Mues et al. | |
| 4,855,496 A | 8/1989 | Anderson et al. | |
| 4,902,828 A * | 2/1990 | Wickenhaeuser et al. ... 562/577 |
| 5,488,129 A | 1/1996 | Huser et al. | |
| 5,512,695 A | 4/1996 | Kreutzer et al. | |
| 5,512,696 A | 4/1996 | Kreutzer et al. | |
| 5,523,453 A | 6/1996 | Breikss | |
| 5,693,843 A | 12/1997 | Breikss et al. | |
| 5,723,641 A | 3/1998 | Tam et al. | |
| 5,821,378 A | 10/1998 | Foo et al. | |
| 5,847,191 A | 12/1998 | Bunel et al. | |
| 5,856,555 A | 1/1999 | Huser et al. | |
| 5,859,302 A | 1/1999 | Park | |
| 5,959,135 A | 9/1999 | Garner et al. | |
| 5,981,772 A | 11/1999 | Foo et al. | |
| 6,020,516 A | 2/2000 | Foo et al. | |
| 6,054,609 A * | 4/2000 | Yokota et al. ............. 562/434 |
| 6,096,680 A | 8/2000 | Park | |
| 6,127,567 A | 10/2000 | Garner et al. | |
| 6,130,347 A | 10/2000 | Julius et al. | |
| 6,171,996 B1 | 1/2001 | Garner et al. | |
| 6,197,992 B1 | 3/2001 | Fischer et al. | |
| 6,242,633 B1 | 6/2001 | Fischer et al. | |
| 6,355,833 B2 | 3/2002 | Fischer et al. | |
| 6,380,421 B1 | 4/2002 | Lu et al. | |
| 6,403,725 B1 * | 6/2002 | Huang et al. ............ 525/326.9 |
| 6,440,891 B1 | 8/2002 | Maas et al. | |
| 6,521,778 B1 | 2/2003 | Fischer et al. | |
| 2002/0169331 A1 * | 11/2002 | Miura et al. ................ 552/1 |
| 2004/0073035 A1 | 4/2004 | Maase et al. | |

FOREIGN PATENT DOCUMENTS

| | | |
|---|---|---|
| DE | 32 48 483 A1 | 7/1984 |
| DE | 35 02 106 A1 | 7/1986 |
| DE | 197 24 884 | 12/1998 |
| DE | 198 26 936 | 12/1999 |
| DE | 198 50 624 A1 | 5/2000 |
| DE | 101 48 712 A1 | 4/2003 |
| DE | 101 56 292 A1 | 5/2003 |

(Continued)

OTHER PUBLICATIONS

U.S. Appl. No. 11/718,518, filed May 3, 2007, Sesing et al.
Hollemann-Wilberg, Lehrbuch der Anorganischen Chemie, 91.-100., Auflage, Walter de Gruyter, Berlin, New York, pp. 235-239 (10985), undated.
George A. Olah, Friedel-Crafts and Related Reactions, vol. 1, pp. 191-197, 201 and 284-290 (1963).
C. Reichardt, Solvent Effects in Organic Chemistry, Weinheim: VCH, XI (Monographs in Modern Chemistry; 3) ISBN 3-527-25793-4), pp. 241-242 (1979).

(Continued)

*Primary Examiner*—Joseph Drodge
(74) *Attorney, Agent, or Firm*—Oblon, Spivak, McClelland, Maier & Neustadt, P.C.

(57) ABSTRACT

A process for removing acids from reaction mixtures using an auxiliary base, in which the auxiliary base: combines with the acid to form a salt which is liquid at temperatures at which the product of value does not significantly decompose during the removal of the liquid salt, and the salt of the auxiliary base with the product of value or the solution of the product of value in a suitable solvent forms two immiscible liquid phases.

23 Claims, No Drawings

FOREIGN PATENT DOCUMENTS

| | | |
|---|---|---|
| EP | 0 181 078 A1 | 5/1986 |
| EP | 0 838 447 A1 | 4/1998 |
| EP | 1 142 898 | 10/2001 |
| FR | 2 810 666 | 12/2001 |
| FR | 2 810 668 | 12/2001 |
| WO | WO 98/13983 | 4/1998 |
| WO | WO 98/27054 | 6/1998 |
| WO | WO 99/46044 | 9/1999 |
| WO | WO 99/64155 | 12/1999 |
| WO | WO 00/16902 | 3/2000 |
| WO | WO 01/14392 A1 | 3/2001 |
| WO | WO 01/74487 * | 10/2001 |

OTHER PUBLICATIONS

Chojnowski, et al., Heteroatom Chemistry, vol. 2, No. 1, pp. 63-70 (1991).
Jerry March, Advance Organic Chemistry, 3$^{rd}$ Edition, John Wiley and Sons, New York, pp. 294, 334 and 347 (1985).
Derwent Publication, 2002-361923/39 (DE 100 38 387) Aug. 2, 2000 (English abstract only).
Derwent Publication, 2002-464340/50 (DE 100 46 025) Sep. 18, 2000 (English abstract only).
Derwent Publication, AN 2003-430329 (DE 101 50 281) Apr. 30, 2003 (English abstract only).
Derwent Publication, AN 2003-450480 (DE 101 50 285) Apr. 17, 2003 (English abstract only).
Derwent Publication, AN 2003-450481 (DE 101 50 286) Apr. 17, 2003 (English abstract only).
W.T. Dye., Jr., J. Am. Chem. Soc., vol. 70, pp. 2595-2596 (1948).
E.L. Gefter, Zh. Obshch. Khim., vol. 28, pp. 1398-1399 (1958).
K.R. Seddon, J. Chem. Tech. Biotechnol., vol. 68, pp. 351-356 (1997).

* cited by examiner

METHOD FOR THE SEPARATION OF ACIDS FROM CHEMICAL REACTION MIXTURES BY MEANS OF IONIC FLUIDS

The present invention describes a process for simplified removal of acids from reaction mixtures using an ionic liquid.

The chemist skilled in the art often has the problem of scavenging acids released during a chemical reaction or removing acids from reaction mixtures. Examples of reactions in which acids are released in the course of the reaction include the silylation of alcohols or amines using halosilanes, the phosphorylation of amines or alcohols using phosphorus halides, the formation of sulfonate esters or sulfonamides from alcohols or amines and sulfonyl chlorides or sulfonic anhydrides, eliminations and substitutions.

These reactions release acids, and for this reason an auxiliary base is additionally added which in general does not take part in the actual reaction as a reactant. It is generally necessary to bind the released acids to this base by salt formation, in order to prevent side reactions and subsequent reactions, or else simply in order to remove the acid from the desired reaction product and optionally return it to the process. When the salts of the bases used are not removed at first, they may also be worked up in the presence of the product of value, e.g. by addition of a further stronger base, such as aqueous alkalis, e.g. sodium hydroxide or potassium hydroxide. This results in the formation of the salt of the stronger base added in this step. Also, the originally used base is liberated. These two components, i.e. the salt of the stronger base and the liberated initially used base (auxiliary base), generally have to be likewise removed from the product of value. This procedure often has the disadvantage that the product of value which is present in the workup may decompose as a result of the added stronger base itself or further materials in this base, e.g. the water in an aqueous alkali.

The salts of the auxiliary base with the acid are generally insoluble in organic solvents and have high melting points, so that they form suspensions in organic media which are more difficult to handle than, for example, liquids. It would therefore be desirable to be able to remove the salts of the auxiliary bases in liquid form. This would also eliminate the known process-engineering disadvantages of suspensions. These are, e.g., the formation of encrustations, reduction of heat transfer, poor mixing and stirrability, and also the formation of localized high and low concentrations and hot spots.

The prior art as it relates to industrially operated processes accordingly has the following disadvantages:
1) the addition of two auxiliary materials, the auxiliary base and also a further strong base, and the consequent need to separate two auxiliary materials from the product of value and from each other,
2) handling of suspensions
3) removal of the salt of the strong base as a solid.

However, a phase separation by means of a liquid-liquid phase separation which is simple from a process-engineering point of view would be desirable.

DE-A 197 24 884 and DE-A 198 26 936 disclose processes for preparing carbonyldiimidazoles by phosgenation of imidazoles, which involve removing the resulting hydrochloride of the imidazole used as starting material as a melt from the reaction mixture. DE-A 198 26 936 discloses at page 3, line 5 that the hydrochloride of the imidazole is surprisingly liquid at temperatures of from 110 to 130° C. and melts well below the literature melting point of 158 to 161° C. The inventors suggest that the reason for this is either the formation of a eutectic mixture of the imidazole hydrochloride with the carbonyldiimidazole product of value or the formation of a ternary mixture of the imidazole hydrochloride, the carbonyldiimidazole product of value and the chlorobenzene solvent. Although the imidazole hydrochloride should not have been liquid, this was surprisingly the case in this specific case. The applicability of this concept for reactions other than phosgenation of imidazoles is not described.

It is an object of the present invention to provide a simplified process for removing acids for other chemical reactions or for the removal of acids which are present in mixtures but are not separated off during a chemical reaction by removing a salt formed from an added auxiliary base and an acid by a liquid-liquid phase separation which is simple from a process-engineering point of view.

We have found that this object is achieved by a process for removing acids from reaction mixtures using an auxiliary base, which comprises the auxiliary base
b) combining with the acid to form a salt which is liquid at temperatures at which the product of value does not significantly decompose during the removal of the liquid salt, and
c) the salt of the auxiliary base with the product of value or the solution of the product of value in a suitable solvent forming two immiscible liquid phases.

It is known to those skilled in the art that the separation of a liquid phase from a second liquid phase is considerably easier to effect from a process-engineering point of view than a solid separation.

The industrial utility of the process of the invention results from the ability to carry out the removal of the auxiliary material by a simple liquid-liquid phase separation, so that the handling of solids which is inconvenient from a process-engineering point of view is unnecessary.

The workup of the auxiliary materials may take place in the absence of the product of value, so that the latter is subject to less stress.

The stated object is achieved by the invention described here. This is accomplished by auxiliary bases being present in the reaction mixtures or being added subsequently, and their salts with acids, which are released in the course of the reaction or added, i.e. not released during the reaction under the reaction conditions and/or workup conditions, being liquid and forming a phase which is immiscible with any dissolved product of value. Such liquid salts are often referred to as ionic liquids. The acids to be bound may either be free in the reaction mixture or form a complex or an adduct with the product of value or another material present in the reaction mixture. Lewis acids in particular tend to form complexes with materials such as ketones. These complexes may be broken by the auxiliary base, which according to this invention results in the formation of the salt from the auxiliary base and the Lewis acid to be removed.

The auxiliary bases may be inorganic or organic bases, preferably organic.

Mixtures or solutions of auxiliary bases may also be used to achieve the object.

Immiscible means that at least two liquid phases, which are separated by a phase boundary, are formed.

When the pure product of value is entirely or substantially miscible with the salt formed by the auxiliary base and the acid, an auxiliary material, e.g. a solvent, may be added to the product of value, in order to achieve separation or solubility reduction. This is sensible when, for example, the solubility of the salt in the product of value or vice versa is 20% by weight or more, preferably 15% by weight or more, more preferably 10% by weight or more and most preferably 5% by weight or more. The solubility is determined under the conditions of each separation. Preference is given to determining the solubility at a temperature above the melting point of the salt and below the lowest of the following temperatures, more preferably 10° C. below the lowest and most preferably 20° C. below the lowest:

boiling point of the product of value boiling point of the solvent temperature of significant decomposition of the product of value The solvent may be regarded as suitable when the mixture of the product of value and the solvent is able to dissolve the salt, or the salt is able to dissolve the product of value or a mixture of product of value and solvent, to a lesser extent than the above-stated quantities. Examples of useful solvents include benzene, toluene, o-, m- or p-xylene, cyclohexane, cyclopentane, pentane, hexane, heptane, octane, petroleum ether, acetone, isobutyl methyl ketone, diethyl ketone, diethyl ether, tert-butyl methyl ether, tert-butyl ethyl ether, tetrahydrofuran, dioxane, ethyl acetate, methyl acetate, dimethylformamide, dimethyl sulfoxide, acetonitrile, chloroform, dichloromethane, methylchloroform or mixtures thereof.

The product of value is generally a nonpolar organic or inorganic compound.

Chemical reactions which form the basis of the invention include all reactions in which acids are released, with the exception of phosgenations, more preferably with the exception of acylations, i.e. reactions of acid halides and carboxylic anhydrides.

Examples of reactions in which the process of the invention may be applied include alkylations using alkyl or aralkyl halides, e.g. methyl chloride, methyl iodide, benzyl chloride, 1,2-dichloroethane or 2-chloroethanol, acylations, i.e. reactions of acid halides and carboxylic anhydrides, of any desired substrates, for example alcohols or amines, silylations, i.e. reactions with compounds which contain at least one Si-Hal bond, e.g. $SiCl_4$, $(H_3C)_2SiCl_2$ or trimethylsilyl chloride, phosphorylations, i.e. reactions with compounds which contain at least one P-Hal bond, e.g. $PCl_3$, $PCl_5$, $POCl_3$, $POBr_3$, dichlorophenylphosphine or diphenylchlorophosphine, as likewise described, for example, by Chojnowski et al., loc cit., sulfurizations, i.e. sulfidations, sulfations, sulfonations and sulfatations, for example using sulfuryl chloride ($SO_2Cl_2$), thionyl chloride ($SOCl_2$), chlorosulfonic acid ($ClSO_3H$), sulfonyl halides, e.g. p-toluenesulfonyl chloride, methanesulfonyl chloride or trifluoromethanesulfonyl chloride, or sulfonic anhydrides, as described, e.g. by Dobrynin, V. N. et al. Bioorg. Khim. 9(5), 1983, 706-10, eliminations, where a C=C double bond is formed with elimination of an acid, for example HCl, HBr, acetic acid or para-toluenesulfonic acid, or deprotonations, where an acidic hydrogen atom is abstracted from the auxiliary base.

Among the mentioned reaction types, preference is given to alkylations, silylations, phosphorylations, sulfurizations, acylations with the exception of phosgenations and eliminations, and particular preference to silylations, phosphorylations and sulfurizations.

According to the invention, an acid may also be removed from reaction mixtures where an acid which was not released during the reaction was added, for example in order to adjust the pH or to catalyze a reaction. This allows, e.g. Lewis acids, which are used as catalysts for Friedel-Crafts alkylations or acylations, to be removed in a simple way.

The acids to be removed according to this invention may be Brönsted or Lewis acids. The naming of acids as Brönsted and Lewis acids is described in Hollemann-Wiberg, Lehrbuch der Anorganischen Chemie, 91st-100th edition, Walter de Gruyter, Berlin N.Y. 1985, p. 235 and 239. The Lewis acids according to this invention also include the Lewis acids used as Friedel-Crafts catalysts, which are described in George A. Olah, Friedel-Crafts and Related Reactions, Vol. I, 191 to 197, 201 and 284-90 (1963). Examples include aluminum trichloride ($AlCl_3$), iron(III) chloride ($FeCl_3$), aluminum tribromide ($AlBr_3$) and zinc chloride ($ZnCl_2$).

In general, the Lewis acids which can be removed according to the invention comprise cationic forms of the metals of groups Ib, IIb, IIIa, IIIb, IVa, IVb, Va, Vb, VIb, VIIb and VIII of the Periodic Table of the Elements or else of the rare earths, for example lanthanum, cerium, praseodymium, neodymium, samarium, europium, gadolinium, terbium, dysprosium, holmium, erbium, thulium, ytterbium or lutetium.

Particular examples include zinc, cadmium, beryllium, boron, aluminum, gallium, indium, thallium, titanium, zirconium, hafnium, erbium, germanium, tin, vanadium, niobium, scandium, yttrium, chromium, molybdenum, tungsten, manganese, rhenium, palladium, thorium, iron, copper and cobalt. Preference is given to boron, zinc, cadmium, titanium, tin, iron and cobalt. Useful counterions of the Lewis acid include $F^-$, $Cl^-$, $ClO^-$, $ClO_3^-$, $ClO_4^-$, $Br^-$, $I^-$, $IO_3^-$, $CN^-$, $OCN^-$, $SCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, dithiocarbamate, salicylate, $(OC_nH_{2n+1})^-$, $(C_nH_{2n-1}O_2)^-$, $(C_nH_{2n-3}O_2)^-$ and $(C_{n+1}H_{2n-2}O_4)^{2-}$, where n is a number from 1 to 20, methanesulfonate ($CH_3SO_3^-$), trifluoromethanesulfonate ($CF_3SO_3^-$), toluenesulfonate ($CH_3C_6H_4SO_3^-$), benzenesulfonate ($C_6H_5SO_3^-$), hydroxide ($OH^-$), anions of aromatic acids such as benzoic acid, phthalic acid and the like, and 1,3-dicarbonyl compounds.

Further examples include carboxylates, and mention should be made in particular of formate, acetate, trifluoroacetate, propionate, hexanoate and 2-ethylhexanoate, stearate and also oxalate, acetylacetonate, tartrate, acrylate and methacrylate, preferably formate, acetate, propionate, oxalate, acetylacetonate, acrylate and methacrylate.

Further useful Lewis acids include borohydrides and organoboron compounds of the general formula $BR''''_3$ and $B(OR'''')_3$, where each R'''' is independently hydrogen, $C_1$-$C_{18}$-alkyl, or $C_2$-$C_{18}$-alkyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or two of them combine to form an unsaturated, saturated or aromatic ring which is optionally interrupted by one or more oxygen and/or sulfur atoms and/or by one or more substituted or unsubstituted imino groups, and the stated radicals in each case may be substituted by functional groups, aryl, alkyl, aryloxy, alkyloxy, halogen, heteroatoms and/or heterocycles. The R'''' radicals may also be bonded to each other.

In addition to the above-cited AlCl₃, FeCl₃, AlBr₃ and ZnCl₂, preferred examples of Lewis acids include BeCl₂, ZnBr₂, ZnI₂, ZnSO₄, CuCl₂, CuCl, Cu(O₃SCF₃)₂, CoCl₂, CoI₂, FeI₂, FeCl₂, FeCl₂(THF)₂, TiCl₄(THF)₂, TiCl₄, TiCl₃, ClTi(OiPr)₃, SnCl₂, SnCl₄, Sn(SO₄), Sn(SO₄)₂, MnCl₂, MnBr₂, ScCl₃, BPh₃, BCl₃, BBr₃, BF₃.OEt₂, BF₃.OMe₂, BF₃.MeOH, BF₃.CH₃COOH, BF₃.CH₃CN, B(CF₃COO)₃, B(OEt)₃, B(OMe)₃, B(OiPr)₃, PhB(OH)₂, 3-MeO-PhB(OH)₂, 4-MeO-PhB(OH)₂, 3-F-PhB(OH)₂, 4-F-PhB(OH)₂, (C₂H₅)₃Al, (C₂H₅)₂AlCl, (C₂H₅)AlCl₂, (C₈H₁₇)AlCl₂, (C₈H₁₇)₂AlCl, (iso-C₄H₉)₂AlCl, Ph₂AlCl, PhAlCl₂, Al(acac)₃, Al(OiPr)₃, Al(OnBu)₃, Al(OsecBu)₃, Al(OEt)₃, GaCl₃, ReCl₅, ZrCl₄, NbCl₅, VCl₃, CrCl₂, MoCl₅, YCl₃, CdCl₂, CdBr₂, SbCl₃, SbCl₅, BiCl₃, ZrCl₄, UCl₄, LaCl₃, CeCl₃, Er(O₃SCF₃), Yb(O₂CCF₃)₃, SmCl₃, SmI₂, B(C₆H₅)₃, TaCl₅.

The Lewis acids may be stabilized by alkali metal or alkaline earth metal halides, for example LiCl or NaCl. To this end, the alkali metal or alkaline earth metal halides are mixed with the Lewis acid in a molar ratio of 0-100:1.

In this context, halogen or Hal refers to fluorine (F), chlorine (Cl), bromine (Br) or iodine (I), preferably chlorine.

In the case of a silylation, phosphorylation or sulfurization, compounds are generally converted which have at least one free O—H, S—H or N—H bond, optionally after deprotonation by the auxiliary base.

Useful auxiliary bases according to the invention include compounds which b) combine with the acid released during the reaction to form a salt which is liquid at temperatures at which the product of value substantially does not decompose during the removal of the liquid salt, and c) the salt of the auxiliary base with the product of value or the solution of the product of value in a suitable solvent forms two immiscible liquid phases.

Preference is given to such auxiliary bases which a) do not take part as a reactant in the reaction.

It is further preferred for this auxiliary base to additionally d) simultaneously function as a nucleophilic catalyst in the reaction, i.e. increase the reaction rate of the reaction compared to the operation in the absence of an auxiliary base by at least 1.5 times, preferably by at least two times, more preferably by about five times, most preferably by at least ten times and especially by at least twenty times.

Such compounds which may be used as bases may contain phosphorus, sulfur or nitrogen atoms, for example at least one nitrogen atom, preferably one to ten nitrogen atoms, more preferably one to five, most preferably one to three and especially one to two. Further heteroatoms, e.g. oxygen, sulfur or phosphorus atoms, may also be present.

Preference is given to such compounds which contain at least one five- to six-membered heterocycle which contains at least one nitrogen atom and also optionally an oxygen or sulfur atom, greater preference to such compounds which contain at least one five- to six-membered heterocycle which contains one, two or three nitrogen atoms and a sulfur or oxygen atom, and greatest preference is given to those with two nitrogen atoms.

Greater preference is given to such compounds which have a molecular weight below 1000 g/mol, greatest preference to below 500 g/mol and especially to below 250 g/mol.

Preference is also given to such compounds usable as bases selected from the compounds of the formulae (Ia) to (Ir),

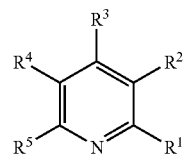

(a)

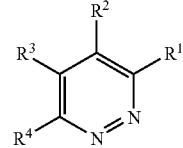

(b)

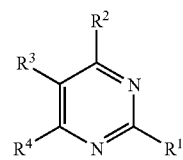

(c)

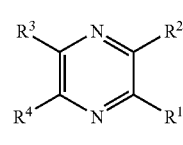

(d)

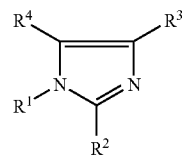

(e)

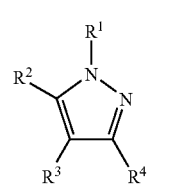

(f)

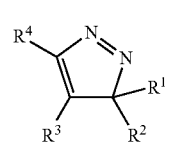

(g)

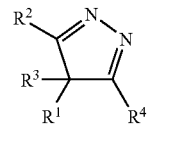

(h)

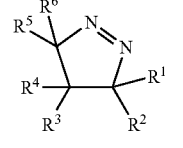

(i)

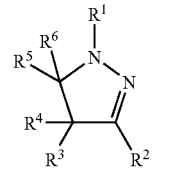

(j)

-continued (k) 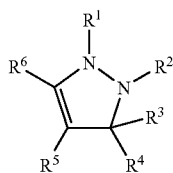

(l) 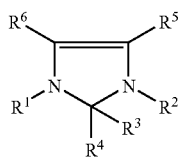

(m) 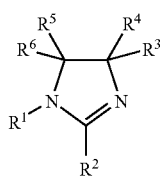

(n) 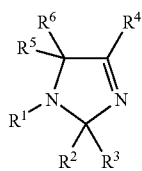

(o) 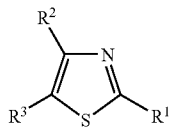

(p) 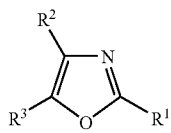

(q) 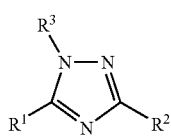

(r) 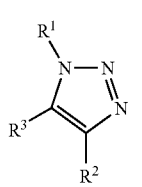

and also oligomers or polymers which contain these structures, where $R^1$, $R^2$, $R^3$, $R^4$, $R^5$ and $R^6$ are each independently hydrogen, $C_1$-$C_{18}$-alkyl, or $C_2$-$C_{18}$-alkyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or two of them combine to form an unsaturated, saturated or aromatic ring which is optionally interrupted by one or more oxygen and/or sulfur atoms and/or by one or more substituted or unsubstituted imino groups, and the stated radicals in each case may be substituted by functional groups, aryl, alkyl, aryloxy, alkyloxy, halogen, heteroatoms and/or heterocycles.

Therein, examples of definitions of $C_1$-$C_{18}$-alkyl which is optionally substituted by functional groups, aryl, alkyl, aryloxy, alkyloxy, halogen, heteroatoms and/or heterocycles include methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)-ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl and $C_2$-$C_{18}$-alkyl which is optionally interrupted by one or more oxygen and/or sulfur atoms and/or one or more substituted or unsubstituted imino groups include 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

When two radicals form a ring, these radicals combined may be 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of the oxygen and/or sulfur atoms and/or imino groups is not limited. In general, it is not more than 5 in the radical, preferably not more than 4 and most preferably not more than 3.

Also, at least one carbon atom, preferably at least two, are generally located between two heteroatoms.

Substituted and unsubstituted imino groups may, for example, be imino, methylimino, iso-propylimino, n-butylimino or tert-butylimino.

Furthermore, functional groups include carboxyl, carboxamide, hydroxyl, di($C_1$-$C_4$-alkyl)amino, $C_1$-$C_4$-alkyloxycarbonyl, cyano or $C_1$-$C_4$-alkyloxy, examples of $C_6$-$C_{12}$-aryl which may optionally be substituted by functional groups, aryl, alkyl, aryloxy, alkyloxy, halogen, heteroatoms and/or heterocycles include phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, iso-propylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl and ethoxymethylphenyl, examples of $C_5$-$C_{12}$-cycloalkyl which is optionally substituted by functional groups, aryl, alkyl, aryloxy, alkyloxy, halogen, heteroatoms and/or heterocycles include cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl and also a saturated or unsaturated bicyclic system, e.g. norbornyl or norbornenyl, examples of a five- to six-membered, oxygen, nitrogen and/or sulfur atom-containing heterocycle include furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl and tert-butylthiophenyl and examples of $C_1$ to $C_4$-alkyl include methyl, ethyl, propyl, isopropyl, n-butyl, sec-butyl or tert-butyl.

Preference is given to $R^1$, $R^2$, $R^3$, $R^4$, $R^5$ and $R^6$ independently being hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino or chlorine.

Greater preference is given to such pyridines (Ia) where one of the radicals $R^1$ to $R^5$ is methyl, ethyl or chlorine and the rest are all hydrogen, or $R^3$ is dimethylamino and the rest are hydrogen or all of them are hydrogen or $R^2$ is carboxyl or carboxamide and all the others are hydrogen or $R^1$ and $R^2$ combined or $R^2$ and $R^3$ combined are 1,4-buta-1,3-dienylene and all the others are hydrogen.

Greater preference is given to such pyridazines (Ib) where one of the radicals $R^1$ to $R^4$ is methyl or ethyl and all the rest are hydrogen or all of them are hydrogen.

Greater preference is given to such pyrimidines (Ic) where $R^2$ to $R^4$ are hydrogen or methyl and $R^1$ is hydrogen, methyl or ethyl, or $R^2$ and $R^4$ are methyl, $R^3$ is hydrogen and $R^1$ is hydrogen, methyl or ethyl.

Greater preference is given to such pyrazines (Id) where $R^1$ to $R^4$ are all methyl or all hydrogen.

Greater preference is given to such imidazoles (Ie) where, independently, $R^1$ is selected from methyl, ethyl, n-propyl, n-butyl, n-pentyl, n-octyl, 2-hydroxyethyl or 2-cyanoethyl and $R^2$ to $R^4$ are each independently hydrogen, methyl or ethyl.

Greater preference is given to such 1H-pyrazoles (If) where, independently, $R^1$ is selected from hydrogen, methyl and ethyl, $R^2$, $R^3$ and $R^4$ are each selected from hydrogen and methyl.

Greater preference is given to such 3H-pyrazoles (Ig) where, independently, $R^1$ is selected from hydrogen, methyl and ethyl, $R^2$, $R^3$ and $R^4$ are each selected from hydrogen and methyl.

Greater preference is given to such 4H-pyrazoles (Ih) where, independently, $R^1$ to $R^4$ are each selected from hydrogen and methyl.

Greater preference is given to such 1-pyrazolines (Ii) where, independently, $R^1$ to $R^6$ are each selected from hydrogen and methyl.

Greater preference is given to such 2-pyrazolines (Ij) where, independently, $R^1$ is selected from hydrogen, methyl, ethyl and phenyl and $R^2$ to $R^6$ are each selected from hydrogen and methyl.

Greater preference is given to such 3-pyrazolines (Ik) in which, independently, $R^1$ and $R^2$ are each selected from hydrogen, methyl, ethyl and phenyl and $R^3$ to $R^6$ are each selected from hydrogen or methyl.

Greater preference is given to such imidazolines (Il) where, independently, $R^1$ and $R^2$ are each selected from hydrogen, methyl, ethyl, n-butyl and phenyl and $R^3$ and $R^4$ are each selected from hydrogen, methyl and ethyl and $R^5$ and $R^4$ are each selected from hydrogen and methyl.

Greater preference is given to such imidazolines (Im) where, independently, $R^1$ and $R^2$ are each selected from hydrogen, methyl and ethyl and $R^3$ to $R^6$ are each selected from hydrogen and methyl.

Greater preference is given to such imidazolines (In) where, independently, $R^1$, $R^2$ and $R^3$ are each selected from hydrogen, methyl and ethyl and $R^4$ to $R^6$ are each selected from hydrogen and methyl.

Greater preference is given to such thiazoles (Io) or oxazoles (Ip) where, independently, $R^1$ is selected from hydrogen, methyl, ethyl and phenyl and $R^2$ and $R^3$ are selected from hydrogen and methyl.

Greater preference is given to such 1,2,4-triazoles (Iq) where, independently, $R^1$ and $R^2$ are each selected from hydrogen, methyl, ethyl and phenyl and $R^3$ is selected from hydrogen, methyl and phenyl.

Greater preference is given to such 1,2,3-triazoles (Ir) where, independently, $R^1$ is selected from hydrogen, methyl and ethyl and $R^2$ and $R^3$ are selected from hydrogen and methyl or $R^2$ and $R^3$ combined are 1,4-buta-1,3-dienylene and all others are hydrogen.

Among these, preference is given to the pyridines and the imidazoles.

Greatest preference is given to the bases 3-chloropyridine, 4-dimethylaminopyridine, 2-ethyl-4-aminopyridine, 2-methylpyridine (α-picoline), 3-methylpyridine (β-picoline), 4-methylpyridine (γ-picoline), 2-ethylpyridine, 2-ethyl-6-methylpyridine, quinoline, isoquinoline, 1-$C_1$-$C_4$-alkylimidazole, 1-methylimidazole, 1,2-dimethylimidazole, 1-n-butylimidazole, 1,4,5-trimethylimidazole, 1,4-dimethylimidazole, imidazole, 2-methylimidazole, 1-butyl-2-methylimidazole, 4-methylimidazole, 1-n-pentylimidazole, 1-n-hexylimidazole, 1-n-octyl imidazole, 1-(2'-aminoethyl)imidazole, 2-ethyl-4-methylimidazole, 1-vinylimidazole, 2-ethylimidazole, 1-(2'-cyanoethyl)imidazole and benzotriazole.

Special preference is given to 1-n-butylimidazole, 1-methylimidazole, 2-methylpyridine and 2-ethylpyridine.

Further suitable bases include tertiary amines of the formula (XI)

where $R^a$, $R^b$ and $R^c$ are each independently $C_1$-$C_{18}$-alkyl, or $C_2$-$C_{18}$-alkyl, $C_6$-$C_{12}$-aryl or $C_1$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or two of them combine to form an unsaturated, saturated or aromatic ring which is optionally interrupted by one or more oxygen and/or sulfur atoms and/or by one or more substituted or unsubstituted imino groups, and the stated radicals in each case may be substituted by functional groups, aryl, alkyl, aryloxy, alkyloxy, halogen, heteroatoms and/or heterocycles, with the proviso that at least two of the three radicals $R^a$, $R^b$ and $R^c$ are different and the radicals $R^a$, $R^b$ and $R^c$ together have at least 8, preferably at least 10, more preferably at least 12 and most preferably at least 13, carbon atoms.

$R^a$, $R^b$ and $R^c$ are preferably each independently $C_1$-$C_{18}$-alkyl, $C_6$-$C_{12}$-aryl or $C_5$-$C_{12}$-cycloalkyl and more preferably $C_1$-$C_{18}$-alkyl, and the stated radicals in each case may be substituted by functional groups, aryl, alkyl, aryloxy, alkyloxy, halogen, heteroatoms and/or heterocycles.

Examples of the particular groups have already been listed above.

Preferred meanings for the $R^a$, $R^b$ and $R^c$ radicals include methyl, ethyl, n-propyl, isopropyl, n-butyl, sec-butyl, tert-butyl, n-pentyl (n-amyl), 2-pentyl (sec-amyl), 3-pentyl, 2,2-dimethylprop-1-yl (neopentyl), n-hexyl, n-heptyl, n-octyl, isooctyl, 2-ethylhexyl, 1,1-dimethylpropyl, 1,1-dimethylbutyl, benzyl, 1-phenylethyl, 2-phenylethyl, α,α-dimethylbenzyl, phenyl, tolyl, xylyl, α-naphthyl, β-naphthyl, cyclopentyl or cyclohexyl.

When two of the $R^a$, $R^b$ and $R^c$ radicals form a chain, this may be, for example, 1,4-butylene or 1,5-pentylene.

Examples of tertiary amines of the formula (XI) include diethyl-n-butylamine, diethyl-tert-butylamine, diethyl-n-pentylamine, diethylhexylamine, diethyloctylamine, diethyl-(2-ethylhexyl)-amine, di-n-propylbutylamine, di-n-propyl-n-pentylamine, di-n-propylhexylamine, di-n-propyloctylamine, di-n-propyl-(2-ethylhexyl)amine, diisopropylethylamine, diisopropyl-n-propylamine, diisopropylbutylamine, diisopropylpentylamine, diisopropylhexylamine, diisopropyloctylamine, diisopropyl-(2-ethylhexyl)amine, di-n-butylethylamine, di-n-butyl-n-propylamine, di-n-butyl-n-pentylamine, di-n-butylhexylamine, di-n-butyloctylamine, di-n-butyl-(2-ethylhexyl)amine, N-n-butylpyrrolidine, N-sec-butylpyrrolidine, N-tert-butylpyrrolidine, N-n-pentylpyrrolidine, N,N-dimethylcyclohexylamine, N,N-diethylcyclohexylamine, N,N-di-n-butylcyclohexylamine, N-n-propylpiperidine, N-isopropylpiperidine, N-n-butylpiperidine, N-sec-butylpiperidine, N-tert-butyl-piperidine, N-n-pentylpiperidine, N-n-butylmorpholine, N-sec-butylmorpholine, N-tert-butylmorpholine, N-n-pentylmorpholine, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butylbenzylamine, diethylphenylamine, di-n-propylphenylamine and di-n-butylphenylamine.

Preferred tertiary amines (XI) are diisopropylethylamine, diethyl-tert-butylamine, diisopropylbutylamine, di-n-butyl-n-pentylamine, N,N-di-n-butylcyclohexylamine and tertiary amines of pentyl isomers.

Particularly preferred tertiary amines are di-n-butyl-n-pentylamine and tertiary amines of pentyl isomers.

A tertiary amine which is likewise preferred and can be used according to the invention, but in contrast to the above-listed amines has three identical radicals, is triallylamine.

Tertiary amines, preferably of the formula (XI), are generally preferred over heterocyclic compounds, for example of the formula (Ia) to (Ir) when the basicity of the latter auxiliary bases is insufficient for the reaction, for example for eliminations.

Examples of acids with which the bases may form salts include hydroiodic acid (HI), hydrogen fluoride (HF), hydrogen chloride (HCl), nitric acid ($HNO_3$), nitrous acid ($HNO_2$), hydrobromic acid (HBr), carbonic acid ($H_2CO_3$), hydrogen carbonate ($HCO_3^-$), methylcarbonic acid (HO(CO)OCH$_3$), ethylcarbonic acid (HO(CO)OC$_2$H$_5$), n-butylcarbonic acid, sulfuric acid ($H_2SO_4$), hydrogen sulfate ($HSO_4^-$), methylsulfuric acid (HO(SO$_2$)OCH$_3$), ethylsulfuric acid (HO(SO$_2$)OC$_2$H$_5$), phosphoric acid ($H_3PO_4$), dihydrogen phosphate ($H_2PO_4^-$), formic acid (HCOOH), acetic acid ($CH_3COOH$), propionic acid, n- and iso-butyric acid, pivalic acid, para-toluenesulfonic acid, benzenesulfonic acid, benzoic acid, 2,4,6-trimethylbenzoic acid, mandelic acid, methanesulfonic acid, ethanesulfonic acid and trifluoromethanesulfonic acid, preference is given to hydrogen chloride, acetic acid, p-toluenesulfonic acid, methanesulfonic acid, 2,4,6-trimethylbenzoic acid and trifluoromethanesulfonic acid and greater preference to hydrogen chloride.

In a preferred embodiment for removing Brönsted acids (protic acids), they are removed without large proportions of Lewis acids, i.e. in the removed salt of the acid with the auxiliary base, the molar ratio of Brönsted acids to Lewis acids is greater than 4:1, preferably greater than 5:1, more preferably greater than 7:1, most preferably greater than 9:1 and in particular greater than 20:1.

Preference is given to such auxiliary bases whose salts of auxiliary bases and acids have a melting temperature at which in the course of the removal of the salt as a liquid phase, no significant decomposition of the product of value occurs, i.e. less than 10 mol % per hour, preferably less than 5 mol %/h, more preferably less than 2 mol %/h and most preferably less than 1 mol %/h.

The melting points of the salts of the more preferred auxiliary bases are generally below 160° C., more preferably below 100° C. and most preferably below 80° C.

Among the auxiliary bases, greatest preference is given to such bases whose salts have an $E_T(30)$ value of >35, preferably of >40, more preferably of >42. The $E_T(30)$ value is a measure of the polarity and is described by C. Reichardt in Reichardt, Christian Solvent Effects in Organic Chemistry Weinheim: VCH, 1979.-XI, (Monographs in Modern Chemistry; 3), ISBN 3-527-25793-4 page 241.

A highly preferred base which, for example, fulfills the stated object is 1-methylimidazole. The use of 1-methylimidazole as a base is mentioned, e.g. in DE-A 35 02 106, but its utility as an ionic liquid is not mentioned there.

1-Methylimidazole is additionally effective as a nucleophilic catalyst [Julian Chojnowski, Marek Cypryk, Witold Fortuniak, Heteroatom. Chemistry, 1991, 2, 63-70]. Chojnowski et al. found that 1-methylimidazole in comparison with triethylamine accelerates the phosphorylation of t-butanol by a factor of 33 and the silylation of pentamethyldisiloxanol by a factor of 930.

It was also found that the hydrochloride of 1-methylimidazole has a melting point of about 75° C. and is substantially immiscible with nonpolar organic products of value, e.g. diethoxyphenylphosphine, triethyl phosphite, ethoxydiphenylphosphine, alkylketene dimer, alkoxysilanes or esters, or solvents. For instance, 1-methylimidazole.HCl, in contrast to the polar solvent water, forms two immiscible phases even with acetone. 1-Methylimidazole may at the same time serve as an auxiliary base and a nucleophilic catalyst and is separated as a liquid hydrochloride from organic media by liquid-liquid phase separation which is simple from a process-engineering point of view.

Instead of 1-methylimidazole, 1-butylimidazole may also be used. The hydrochloride of 1-butylimidazole is already liquid at room temperature, so that 1-butylimidazole may be used as an auxiliary base and catalyst for reactions in which materials are handled which are liable to decompose even above room temperature. The acetate and formate of 1-methylimidazole are likewise liquid at room temperature.

Equally, all derivatives of imidazole may be used whose salts have an $E_T(30)$ value of >35, preferably of >40, more preferably of >42 and a melting point at which in the course of removal of the salt as a liquid phase no significant decomposition of the product of value occurs. The polar salts of these imidazoles form two immiscible phases with less polar organic media as described above.

A further highly preferred base which achieves the stated object is 2-ethylpyridine. The use of different pyridines as auxiliary bases is described e.g. in DE 198 50 624, but its utility as an ionic liquid is not recognized there.

Pyridine itself and derivatives of pyridine are known to those skilled in the art as nucleophilic catalysts [Jerry March, "Advanced Organic Chemistry, 3rd Edition, John Wiley & Sons, New York 1985, PP. 294, 334, 347].

It was also found that the hydrochloride of 2-ethylpyridine has a melting point of about 55° C. and is immiscible with nonpolar organic products of value (see above) or solvents. 2-Ethylpyridine may also serve at the same time as an auxiliary base and nucleophilic catalyst and is separated as a liquid hydrochloride from organic media by a liquid-liquid phase separation which is simple from a process-engineering point of view.

Equally, all derivatives of pyridine may be used whose salts have an $E_T(30)$ value of >35, preferably of >40, more preferably of >42 and a melting point at which in the course of removal of the salt as a liquid phase no significant decomposition of the product of value occurs. The polar salts of these pyridines form two immiscible phases with less polar organic media.

The operation of the reaction is not limited and, according to the invention, may be carried out with scavenging of the released or added acids, optionally with nucleophilic catalysis, batchwise or continuously and under air or a protective gas atmosphere.

For temperature-sensitive products of value, it may be sufficient to allow the salt of the auxiliary base and acid to precipitate as a solid salt during the reaction and not to melt it until the workup or following removal of the majority of the product of value in a solid-liquid separation. In this way, the product is subjected to less thermal stress.

The invention further provides a process for removing the above-cited auxiliary bases or auxiliary bases used as nucleophilic catalysts from a reaction mixture by admixing the reaction mixture with at least one mole of acid per mole of auxiliary base. This allows the removal of such auxiliary bases as ionic liquids with the aid of a liquid-liquid separation.

The free base may be recovered from the salt of the auxiliary base recovered from the product of value by the methods known to those skilled in the art and recycled to the process.

This may be carried out, for example, by releasing the salt of the auxiliary base using a strong base, e.g. NaOH, KOH, $Ca(OH)_2$, milk of lime, $Na_2CO_3$, $NaHCO_3$, $K_2CO_3$ or $KHCO_3$, optionally in a solvent, e.g. water, methanol, ethanol, n- or isopropanol, n-butanol, n-pentanol or butanol isomeric mixtures or pentanol isomeric mixtures or acetone. The auxiliary base released in this way may be removed if it forms its own phase or, if it is miscible with the salt of the stronger base or the solution of the salt of the stronger base, it may be removed from the mixture by distillation. If necessary, the released auxiliary base may also be removed from the salt of the stronger base or the solution of the salt of the stronger base by extraction using an extractant. Extractants are, for example, solvents, alcohols or amines.

If necessary, the auxiliary base may be washed with water or aqueous NaCl or $Na_2SO_4$ solution and then dried, e.g. by removal of any water present with the aid of an azeotropic distillation using benzene, toluene, xylene, butanol or cyclohexane.

If necessary, the base may be distilled before it is reused.

A further possibility of recycling is to distill the salt of the auxiliary base which causes the salt to thermally decompose to give its starting materials, i.e. the free base and the scavenged acid. The lower-boiling portion of the salt is distilled off, while the higher-boiling portion remains in the bottom product. The free auxiliary base is either the low- or high-boiler. In this way, e.g. 1-butylimidazole formate is separated distillatively to give formic acid (top product) and 1-butylimidazole (bottom product), as described in EP-A 181 078.

Preferred phosphorylations which can be carried out with the process according to the invention are such reactions in which phosphorus compounds, for example phosphines, phosphinic esters, phosphinous esters (phosphinites), phosphonic esters, phosphonic halides, phosphonic amides, phosphonous esters (phosphonites), phosphonous amides, phosphonous halides, phosphoric esters, phosphoric diester halides, phosphoric diester amides, phosphoric ester dihalides, phosphoric ester diamides, phosphorous esters (phosphites), phosphorous diester halides, phosphorous diester amides, phosphorous ester dihalides or phosphorous ester diamides are formed and an acid is eliminated in the course of the reaction and forms a salt with the auxiliary base as described above.

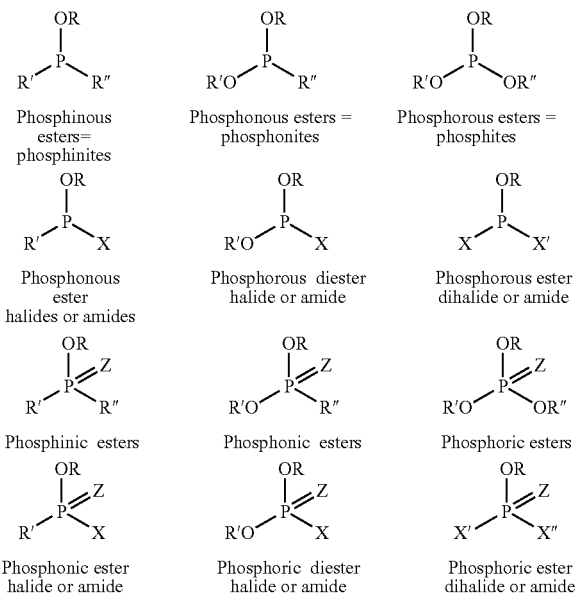

In these formulae, R, R' and R" are each any desired radical, X and X' are each halogen or pseudohalogen, for example F, Cl, Br, I, CN, OCN or SCN, or unsubstituted, monosubstituted or disubstituted amino groups and Z is oxygen, sulfur or an unsubstituted or monosubstituted nitrogen atom.

These phosphorus compounds may have one or more, for example two, three or four, preferably two or three, more preferably two, phosphorus atoms. In such compounds, the phosphorus atoms are typically bonded by a bridge.

Examples of such bridged compounds having two phosphorus atoms include:
diphosphites

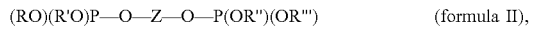
(RO)(R'O)P—O—Z—O—P(OR")(OR''')     (formula II), diphosphonites

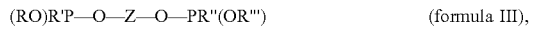
(RO)R'P—O—Z—O—PR"(OR''')     (formula III), diphosphinites

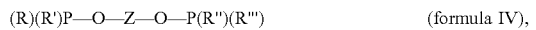
(R)(R')P—O—Z—O—P(R")(R''')     (formula IV), phosphite-phosphonites

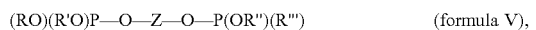
(RO)(R'O)P—O—Z—O—P(OR")(R''')     (formula V), phosphite-phosphinites

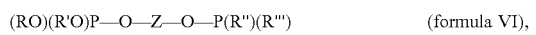
(RO)(R'O)P—O—Z—O—P(R")(R''')     (formula VI), phosphonite-phosphinites

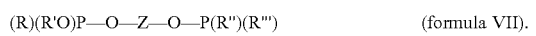
(R)(R'O)P—O—Z—O—P(R")(R''')     (formula VII).

In these formulae, R, R', R" and R''" may be any desired organic radicals and Z may be any desired bivalent bridge.

These radicals may each independently be, for example, linear or branched, substituted or unsubstituted, aromatic or aliphatic radicals each having one to 20 carbon atoms, such as $C_1$-$C_{18}$-alkyl, or $C_2$-$C_{18}$-alkyl, $C_5$-$C_{18}$-alkenyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle, where the stated radicals in each case may be substituted by aryl, alkyl, aryloxy, alkyloxy, heteroatoms and/or heterocycles.

The compounds mentioned may each be symmetrically or unsymmetrically substituted.

Examples of phosphorus compounds having one phosphorus atom include those of the formula (VIII)

$$P(X^1R^7)(X^2R^8)(X^3R^9) \quad \text{(VIII)}$$

where $X^1$, $X^2$ and $X^3$ are each independently oxygen, sulfur, $NR^{10}$ or a single bond $R^7$, $R^8$, $R^9$ and $R^{10}$ are each independently identical or different organic radicals.

Examples of phosphorus compounds having two phosphorus atoms include those of the formula (IX)

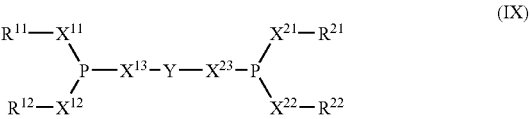

where $X^{11}$, $X^{12}$, $X^{13}$, $X^{21}$, $X^{22}$ and $X^{23}$ are each independently oxygen, sulfur, $NR^{10}$ or a single bond $R^{11}$ and $R^{12}$ are each independently identical or different, individual or bridged organic radicals $R^{21}$ and $R^{22}$ are each independently identical or different, individual or bridged organic radicals, Y is a bridging group The phosphorus compounds described are, for example, suitable as ligands for catalysts for the hydrocyanation of butadiene to a mixture of isomeric pentenenitriles. As well as the hydrocyanation of 1,3-butadienic hydrocarbon mixtures, the catalysts are generally suitable for all common hydrocyanation processes. These include in particular the hydrocyanation of nonactivated olefins, for example of styrene and 3-pentenenitrile. It is also conceivable to use them for hydrogenation, hydroformylation, hydrocarboxylation, hydroamidation, hydroesterification and aldol condensation.

Such catalysts may have one or more phosphorus compounds as ligands. In addition to the phosphorus compounds as ligands, they may also have at least one further ligand selected from cyanide, halides, amines, carboxylates, acetylacetone, aryl- or alkylsulfonates, hydride, CO, olefins, dienes, cycloolefins, nitriles, N-heterocycles, aromatics and heteroaromatics, ethers, $PF_3$ and also mono-, bi- and multidentate phosphine, phosphinite, phosphonite and phosphite ligands. These further ligands may likewise be mono-, bi- or multidentate and coordinate to the metal. Examples of useful further phosphorus ligands include the phosphine, phosphinite and phosphite ligands described previously as the prior art.

The metal is preferably of transition group VIII of the Periodic Table, more preferably cobalt, rhodium, ruthenium, palladium or nickel atoms in any desired oxidation state. When the catalysts according to the invention are used for hydrocyanation, the metal is of transition group VIII of the Periodic Table, in particular nickel.

When nickel is used, it may be in different valencies, such as 0, +1, +2 or +3. Preference is given to nickel(0) and nickel(+2), in particular nickel(0).

Catalysts for hydroformylations generally form the catalytically active species from the catalysts or catalyst precursors used in each case under hydroformylation conditions.

Metals used for this purpose are preferably cobalt, ruthenium, rhodium, palladium, platinum, osmium or iridium and in particular cobalt, rhodium or ruthenium in any desired oxidation stage.

The preparation of these catalysts is costly and inconvenient. This is true in particular because the catalyst systems are gradually destroyed in the course of their use and therefore have to be discharged and replaced by new catalyst.

Processes for preparing the phosphorus compounds and the corresponding catalysts are known per se, for example from U.S. Pat. No. 3,903,120, U.S. Pat. No. 5,523,453, U.S. Pat. No. 5,981,772, U.S. Pat. No. 6,127,567, U.S. Pat. No. 5,693,843, U.S. Pat. No. 5,847,191, WO 01/14392, WO 99/13983 and WO 99/64155.

To prepare the phosphorus compounds used in the catalysts as ligands, a dihalogenphosphorus(III) compound, for example, can be initially reacted with a monoalcohol to give a diester. If desired, this compound may be isolated and/or purified, for example by distillation, before further reaction. This diester is then, for example, reacted with a diol to give the bidentate phosphonite ligand. In the case that symmetric ligands are to be obtained, two equivalents of the diester may be reacted in a one-stage reaction with one equivalent of the diol. Otherwise, one equivalent of the diester is initially reacted with one equivalent of the diol and, after formation of the monocondensation product, a second diol is added and further reacted to the phosphorus compound.

According to the invention, the acid released in the reaction may be scavenged with one of the auxiliary bases specified to form a liquid salt, so that this synthesis may be considerably simplified.

Organodiphosphonites of the formula III, and also catalyst systems which comprise such organodiphosphonites are known, for example from WO 99/64155. For the preparation of such organodiphosphonites of the formula III, WO 99/64155 describes the reaction of R'PCl$_2$ with one mole of ROH and subsequent reaction of the (RO)R'PCl obtained with half a mole, based on one mole of (RO)R'PCl, of a compound HO—Z—OH at a temperature in the range from 40 to about 200° C. The elimination of the hydrogen halide in the first step should preferably be purely thermal. In addition, it should be possible to carry out both steps in the presence of a base.

According to the invention, the prior art processes, for example that of WO 99/64155, for preparing the specified phosphorus compounds are carried out in a similar manner, with the difference that, according to the invention, an auxiliary base is used as described above and the released acid is removed from the reaction mixture with the aid of the auxiliary base, and, as above, the auxiliary base and the acid form a salt which is liquid at temperatures at which the phosphorus compound does not significantly decompose during the removal of the liquid salt and the salt of the auxiliary base with the phosphorus compound or the solution of the phosphorus compound in a suitable solvent form two immiscible liquid phases.

In general, the specified phosphorus compounds may be prepared, for example, as follows:

The reactants are mixed with each other in the desired stoichiometry, optionally dissolved in a solvent or dispersed, i.e. suspended or emulsified. It may be sensible to divide the reactants into one or more compositions, i.e. streams separated from each other, so that the reaction does not take place before mixing. The auxiliary base which, according to the invention, forms a liquid salt with the acid may be added to one or more of these streams or fed to the reaction separately from the streams as a separate stream. It is also possible, although less preferred, not to add the auxiliary base until after the reaction to remove the acid.

The reactants or the compositions specified are fed to a reactor and reacted with each other under reaction conditions which lead to the reaction of the reactants to the product. Such reaction conditions are dependent upon the reactants used and the desired products and specified by the prior art cited in this document.

The reaction may be continuous, semicontinuous or batchwise. The temperature generally ranges from 40° C. to 200° C., and the pressure is not significant according to the invention and may be less than atmospheric, greater than atmospheric or atmospheric, for example from 10 mbar to 10 bar, preferably from 20 mbar to 5 bar, more preferably from 50 mbar to 2 bar and in particular from 100 mbar to 1.5 bar. The residence time of the reaction mixture in the reactor may be from a few seconds to a number of hours and is dependent upon the reaction temperature and, generally to a lesser extent, upon the pressure applied.

The residence time chosen in a continuous reaction at a temperature sufficient for the reaction is preferably short, i.e. from a few seconds to about 2 hours, preferably from 1 second to 2 hours, more preferably from 1 second to 1 hour, even more preferably from 1 second to 30 minutes, in particular from 1 second to 15 minutes and extremely preferably from 1 second to 5 minutes.

In a particularly preferred embodiment, the preparation of the phosphorus compounds, preferably of those having more than one phosphorus atom, more preferably those having 2 or 3 phosphorus atoms and most preferably those having 2 phosphorus atoms, from the respective reactants is carried out continuously at a temperature of from 60° C. to 150° C., preferably at a temperature above the melting point of the salt of the auxiliary base used with the released salt up to 130° C., at a residence time of less than 1 hour, preferably less than 30 minutes, more preferably less than 15 minutes, even more preferably from 1 second to 5 minutes, in particular from 1 second to 1 minute and extremely preferably from 1 to 30 seconds.

Such an embodiment suppresses exchange of substituents on the phosphorus atoms and it is thus possible to prepare compounds under predominantly kinetic control having more than one phosphorus atom, for example compounds of the formula (IX), and phosphorus compounds having mixed substituents, for example compounds of the formula (VII) having different $R^7$, $R^8$ and/or $R^9$ radicals without the substituents being exchanged as a consequence of equilibration on the phosphorus atom or atoms.

During the reaction, good mixing has to be ensured, for example by stirring or circulation by pumping with static mixers or nozzles.

Useful reactors include apparatus known to those skilled in the art per se, for example one or more stirred or tubular reactors in a battery having internal or external heating and preferably reaction mixing pumps.

The reaction effluent is conducted into an apparatus in which the phases formed during the reaction are separated from each other, for example phase separators or mixer-settler apparatus. In this apparatus, a phase separation of the phase which predominantly comprises ionic liquid from the phase which predominantly comprises the desired reaction product is carried out at a temperature at which the salt of auxiliary base with the acid is liquid. If necessary, solvent may be added in order to accelerate a phase separation.

The auxiliary base may, as described above, be recovered from the phase which predominantly comprises ionic liquid.

The reaction product may be isolated and/or purified from the phase which comprises the desired reaction product by methods known per se, for example, by distillation, rectification, extraction, fractional or simple crystallization, membrane separating processes, chromatography or combinations thereof.

The solvent used in the reaction may be one of the above-listed solvents.

The auxiliary base used in the reaction is generally used, based on the amount of acid to be expected, in a stoichiometric amount or slight excess, for example from 100 to 200 mol %, based on the amount of acid to be expected, preferably from 100 to 150 mol % and more preferably from 105 to 125 mol %.

The reactants for preparing the desired phosphorus compounds are known to those skilled in the art per se or are easily deducible and disclosed, for example, in the prior art cited in this document, as are the stoichiometric ratios in order to react the reactants with each other.

If possible, the reactants are used as liquids or melts, and to this end are optionally dissolved in a solvent or dispersed. However, it will be appreciated that it is also possible to use at least some of the reactants in solid form.

When they are admixed with a solvent, the solvent is generally used in such an amount that the mixture is liquid, for example as a solution or dispersion. Typical concentrations of the reactants based on the total amount of the solution or dispersion are from 5 to 95% by weight, preferably from 10 to 90% by weight, more preferably from 25 to 90% by weight and most preferably from 50 to 90% by weight.

Compounds (VIII) are of the formula $$P(X^1R^7)(X^2R^8)(X^3R^9) \quad \text{(VIII)}$$

For the purposes of the present invention, compound (VIII) is a single compound or a mixture of different compounds of the above formula.

According to the invention, $X^1$, $X^2$ and $X^3$ are each independently oxygen, sulfur, $NR^{10}$ or a single bond.

$R^{10}$ is hydrogen or an organic radical having 1-10 carbon atoms, preferably hydrogen, phenyl or $C_1$-$C_4$-alkyl, which in this document is methyl, ethyl, iso-propyl, n-propyl, n-butyl, iso-butyl, sec-butyl and tert-butyl.

When all of the $X^1$, $X^2$ and $X^3$ groups are single bonds, compound (VIII) is a phosphine of the formula $P(R^7R^8R^9)$ where $R^7$, $R^8$ and $R^9$ are each as defined in this description.

When two of the $X^1$, $X^2$ and $X^3$ groups are single bonds and one is oxygen, compound (VIII) is a phosphinite of the formula $P(OR^7)(R^8)(R^9)$ or $P(R^7)(OR^8)(R^9)$ or $P(R^7)(R^8)(OR^9)$ where $R^7$, $R^8$ and $R^9$ are each as defined in this description.

When one of the $X^1$, $X^2$ and $X^3$ groups is a single bond and two are oxygen, compound (VIII) is a phosphonite of the formula $P(OR^7)(OR^8)(R^9)$ or $P(R^7)(OR^8)(OR^9)$ or $P(OR^7)(R^8)(OR^9)$ where $R^7$, $R^8$ and $R^9$ are each as defined in this description.

In a preferred embodiment, all of the $X^1$, $X^2$ and $X^3$ groups should be oxygen, so that compound (VIII) is a phosphite of the formula $P(OR^7)(OR^8)(OR^9)$ where $R^7$, $R^8$ and $R^9$ are each as defined in this description.

According to the invention, $R^7$, $R^8$ and $R^9$ are each independently identical or different organic radicals.

Useful $R^7$, $R^8$ and $R^9$ radicals are independently alkyl radicals, advantageously having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, p-fluorophenyl, 1-naphthyl, 2-naphthyl, or hydrocarbyl, advantageously having from 1 to 20 carbon atoms, such as 1,1'-biphenol or 1,1'-binaphthol.

The $R^7$, $R^8$ and $R^9$ groups may be bonded directly to each other, i.e. not just via the central phosphorus atom. The $R^7$, $R^8$ and $R^9$ groups are preferably not directly bonded to each other.

In a preferred embodiment, useful $R^7$, $R^8$ and $R^9$ groups are radicals selected from the group consisting of phenyl, o-tolyl, m-tolyl and p-tolyl.

In a particularly preferred embodiment, a maximum of two of the $R^7$, $R^8$ and $R^9$ groups should be phenyl groups.

In another preferred embodiment, a maximum of two of the $R^7$, $R^8$ and $R^9$ groups should be o-tolyl groups.

Particularly preferred compounds (VIII) include those of the formula

where w, x, y and z are each a natural number
where w+x+y+z=3 and
w and z are less than or equal to 2, such as (p-tolyl-O—)(phenyl)$_2$P, (m-tolyl-O—)(phenyl)$_2$P, (o-tolyl-O—)(phenyl)$_2$P, (p-tolyl-O—)$_2$(phenyl)P, (m-tolyl-O—)$_2$(phenyl)P, (o-tolyl-O—)$_2$(phenyl)P, (m-tolyl-O—)(p-tolyl-O—)(phenyl)P, (o-tolyl-O—)(p-tolyl-O—)(phenyl)P, (o-tolyl-O—)(m-tolyl-O—)(phenyl)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P (o-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P are obtained by reacting a mixture comprising m-cresol and p-cresol, in particular in a molar ratio of 2:1, as obtained from the destillative workup of crude oil, with a phosphorus trihalide, such as phosphorus trichloride.

Such compounds (VIII) and their preparation are known per se.

Compounds (IX) are of the formula

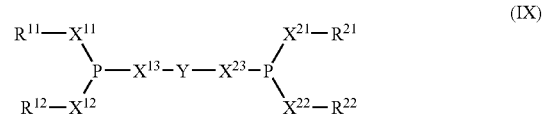

where
$X^{11}$, $X^{12}$, $X^{13}$, $X^{21}$, $X^{22}$ and $X^{23}$ are each independently oxygen, sulfur, $NR^{10}$ or a single bond
$R^{11}$ and $R^{12}$ are each independently identical or different, individual or bridged organic radicals
$R^{21}$ and $R^{22}$ are each independently identical or different, individual or bridged organic radicals,
Y is a bridging group.

For the purposes of the present invention, compound (IX) is a single compound or a mixture of different compounds of the above formula.

In a preferred embodiment, $X^{11}$, $X^{12}$, $X^{13}$ $X^{21}$, $X^{22}$ and $X^{23}$ may each be oxygen. In such a case, the bridging group Y is linked by phosphite groups.

In another preferred embodiment, $X^{11}$ and $X^{12}$ may each be oxygen and $X^{13}$ is a single bond, or $X^{11}$ and $X^{13}$ may be oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ is the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphinite. In such a case, $X^2$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ may be the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

Advantageous bridging groups Y include substituted, for example with $C_1$-$C_4$-alkyl, halogen such as fluorine, chlorine or bromine, halogenated alkyl such as trifluoromethyl, or aryl such as phenyl, or unsubstituted, aryl groups, preferably those having from 6 to 20 carbon atoms in the aromatic system, in particular pyrocatechol, bis(phenol) or bis(naphthol).

The $R^{11}$ and $R^{12}$ radicals may each independently be identical or different organic radicals. The $R^{11}$ and $R^{12}$ radicals are advantageously aryl radicals, preferably those having from 6 to 10 carbon atoms, which may be unsubstituted or mono- or polysubstituted, in particular by $C_1$-$C_4$-alkyl, halogen such as fluorine, chlorine or bromine, halogenated alkyl such as trifluoromethyl, aryl such as phenyl, or unsubstituted aryl groups.

The $R^{21}$ and $R^{22}$ radicals may each independently be identical or different organic radicals. The $R^{21}$ and $R^{22}$ radicals are advantageously aryl radicals, preferably those having from 6 to 10 carbon atoms, which may be unsubstituted or mono- or polysubstituted, in particular by $C_1$-$C_4$-alkyl, halogen such as fluorine, chlorine or bromine, halogenated alkyl such as trifluoromethyl, aryl such as phenyl, or unsubstituted aryl groups.

The $R^{11}$ and $R^{12}$ radicals may be individual or bridged.

The $R^{21}$ and $R^{22}$ radicals may be individual or bridged.

The $R^{11}$, $R^{12}$, $R^{21}$ and $R^{22}$ radicals may all be individual, two may be bridged and two individual or all four may be bridged, in the way described.

In the context of the present disclosure, reference is explicitly made to the extent specified to the following, particularly preferred embodiments:

In a particularly preferred embodiment, useful compounds are those specified in U.S. Pat. No. 3,773,809, in particular those described in column 2, line 23 to column 4, line 14 and in the examples.

In a particularly preferred embodiment, useful compounds are those specified in U.S. Pat. No. 6,127,567, in particular the compounds used in column 2, line 23 to column 6, line 35, in the formulae I, II, III, IV, V, VI, VII, VIII and 1× and in the Examples 1 to 29.

In a particularly preferred embodiment, useful compounds are those specified in U.S. Pat. No. 6,171,996, in particular the compounds used in column 2, line 25 to column 6, line 39, in the formulae I, II, III, IV, V, VI, VII, VII and IX and in the Examples 1 to 29.

In a particularly preferred embodiment, useful compounds are those specified in U.S. Pat. No. 6,380,421, in particular the compounds used in column 2, line 58 to column 6, line 63, in the formulae I, II and III and in the Examples 1 to 3.

In a particularly preferred embodiment, useful compounds are those specified in U.S. Pat. No. 5,488,129, in particular the compounds used in column 3, line 4 to column 4, line 33, in the formula I and in the Examples 1 to 49.

In a particularly preferred embodiment, useful compounds are those specified in U.S. Pat. No. 5,856,555, in particular the compounds used in column 2, line 13 to column 5, line 30, in the formulae I and II and in the Examples 1 to 4.

In a particularly preferred embodiment, useful compounds are those specified in WO 99/46044, particularly the compounds used in page 3, line 7 to page 8, line 27, and in particular those in the formulae Ia to Ig and in the Examples 1 to 6.

In a particularly preferred embodiment, useful compounds are those specified in U.S. Pat. No. 5,723,641 and of the formulae I, I, III, IV and V.

In a particularly preferred embodiment, useful compounds are those specified in U.S. Pat. No. 5,512,696 and of the formulae I, II, III, IV, V, VI and VII, in particular the compounds used there in the Examples 1 to 31.

In a particularly preferred embodiment, useful compounds are those specified in U.S. Pat. No. 5,821,378 and of the formulae I, II, III, IV, V, VI, VII, VIII, IX, X, XI, XII, XIII, XIV and XV, in particular the compounds used there in the Examples 1 to 73.

In a particularly preferred embodiment, useful compounds are those specified in U.S. Pat. No. 5,512,695 and of the formulae I, II, III, IV, V and VI, in particular the compounds used there in the Examples 1 to 6.

In a particularly preferred embodiment, useful compounds are those specified in U.S. Pat. No. 5,981,772 and of the formulae I, I, III, IV, V, VI, VII, VIII, IX, X, XI, XII, XIII and XIV, in particular the compounds used there in the Examples 1 to 66.

In a particularly preferred embodiment, useful compounds are those specified in U.S. Pat. No. 6,020,516 and of the formulae I, II, III, IV, V, VI, VII, VIII, IX and X, in particular the compounds used there in the Examples 1 to 33.

In a particularly preferred embodiment, useful compounds are those specified in U.S. Pat. No. 5,959,135 and the compounds used there in Examples 1 to 13.

In a particularly preferred embodiment, useful compounds are those specified in U.S. Pat. No. 5,847,191 and of the formulae I, II and III.

In a particularly preferred embodiment, useful compounds are those specified in U.S. Pat. No. 5,523,453, in particular the compounds represented there by the formulae 1, 2, 3, 4, 5, 6, 7, 8, 9, 10, 11, 12, 13, 14, 15, 16, 17, 18, 19, 20 and 21.

In a particularly preferred embodiment, useful compounds are those specified in WO 01/14392, preferably the compounds represented in the formulae V, VI, VII, VIII, IX, X, XI, XII, XIII, XIV, XV, XVI, XVII, XXI, XXII, XXIII.

In a particularly preferred embodiment, useful compounds are those specified in WO 98/27054.

In a particularly preferred embodiment, useful compounds are those specified in WO 99/13983, particularly the compounds specified on page 5, line 1 to page 11, line 45 and in particular the compounds specified in the formulae Ia to Ih and in the Examples 1 to 24.

In a particularly preferred embodiment, useful compounds are those specified in WO 99/64155, particularly the compounds specified on page 4, line 1 to page 12, line 7 and in particular the compounds specified in the formulae Ia to Ic and in the Examples 1 to 4.

In a particularly preferred embodiment, useful compounds are those specified in the German patent application DE 10038037.

In a particularly preferred embodiment, useful compounds are those specified in the German patent application DE 10046025.

In a particularly preferred embodiment, useful compounds are those specified in the German patent application having the reference number DE 10156292.6 and the application date Nov. 19, 2001, in particular the compounds specified in the filing text on page 1, lines 6 to 19 and from page 2, line 21 to page 2, line 30.

In a particularly preferred embodiment, useful compounds are those specified in the German patent application having the reference number DE 10150281.8 and the application date Oct. 12, 2001, in particular the compounds specified in the filing text on page 1, line 36 to page 5, line 45.

In a particularly preferred embodiment, useful compounds are those specified in the German patent application having the reference number DE 10150285.0 and the application date Oct. 12, 2001, in particular the compounds specified in the filing text on page 1, line 35 to page 5, line 37.

In a particularly preferred embodiment, useful compounds are those specified in the German patent application having the reference number DE 10150286.9 and the application date Oct. 12, 2001, in particular the compounds specified in the filing text on page 1, line 37 to page 6, line 15.

In a particularly preferred embodiment, useful compounds are those specified in the German patent application having the reference number DE 10148712.6 and the application date Oct. 12, 2001, in particular the compounds specified in the filing text on page 1, lines 6 to 29 and page 2, line 15 to page 4, line 24.

To remove Lewis acids, a complex of an auxiliary base and Lewis acid is formed according to the invention which is, as described above, liquid at the relevant temperatures and forms a phase immiscible with the product of value.

For example, to remove aluminum trichloride, it is known to add equimolar amounts of phosphoryl chloride ($POCl_3$) to the product, and the resulting $Cl_3PO.AlCl_3$ complex precipitates and may be removed, for example, by filtration (W. T. Dye, J. Am. Chem. Soc., 1948, 70, 2595). The same document furthermore discloses the addition of a precisely calculated amount of water to the product in order to form the hydrate of aluminum trichloride which may likewise be removed from product by filitration.

According to Gefter, Zh. Obshch. Khim., 1958, 28, 1338, $AlCl_3$ may also be precipitated by complex formation with pyridine and thus removed.

DE 32 48 483 discloses a process for removing $AlCl_3$ with the aid of NaCl.

A disadvantage of these processes is that these complexes are hygroscopic, as solid complexes require a solid-liquid separation and in this separation often show unfavorable filtration properties, for example lump formation, which makes any subsequent washing more difficult.

EP 838 447 describes the formation of liquid clathrates which are insoluble in the particular Friedel-Crafts product and can be removed, for example, by phase separation.

K. R. Seddon, J. Chem. Tech. Biotechnol. 68 (1997) 351 describes principles of a removal of Lewis acids with the aid of ionic liquids such as 1-butylpyridinium chloride-aluminum(III) chloride, 1-butyl-3-methylimidazolium chloride-aluminum(III) chloride. However, these are permanent cationic systems which, in contrast, for example, to the auxiliary bases (Ia) to (Ir) cannot be used as free, nonionic auxiliary bases.

EP-A1 1 142 898 describes phosphorylations for preparing biphenylphosphonites, in which phases of eutectic pyridine-hydrochloride/pyridine-aluminum chloride mixtures of product-containing solvent phases are removed.

A disadvantage is that the liquid removal of such mixtures from the product is impossible without the formation of a eutectic.

According to the invention, the above-described process for removing Lewis acids from reaction mixtures with the aid of an auxiliary base is carried out by the auxiliary base
b) combining with the Lewis acid to form a salt which is liquid at temperatures at which the product of value does not significantly decompose during the removal of the liquid salt, and
c) the salt of the auxiliary base with the product of value or the solution of the product of value in a suitable solvent forming two immiscible liquid phases.

To this end, the reaction with the Lewis acid to form the product is carried out as is customary and, after the end of the reaction, the auxiliary base is added to the reaction mixture to remove the Lewis acid. It will be appreciated that the reaction mixture may also be added to the auxiliary base. It is important that the reaction mixture mixes with the auxiliary base which generally results in a complex of auxiliary base and Lewis acid forming. For every mole of Lewis acid in the reaction mixture to be removed, generally at least one mole of auxiliary base is used, preferably from 1.0 to 1.5 mol/mol, more preferably from 1.0 to 1.3 mol/mol, even more preferably from 1.0 to 1.3 mol/mol and in particular from 1.0 to 1.25 mol/mol.

After the mixing of the Lewis acid and auxiliary base, further workup may be effected immediately although stirring may also be continued for a few minutes to a few hours, preferably from 5 to 120 minutes, particularly from 10 to 60 minutes and most preferably from 15 to 45 minutes.

The reaction mixture may advantageously be maintained at a temperature at which the complex of auxiliary base and Lewis acid is liquid, but no significant decomposition occurs, although it may also be maintained below the melting temperature of the complex.

The phases are separated under conditions as already described above. In the case of a complex, for example, of $AlCl_3$ and N-methylimidazole, the melting point is about 60°

C., so that the removal, for example by phase separation, from the product of value may follow at relatively low temperatures.

The removal according to the invention may be used in any case where Lewis acids have to be removed from a product of value, preferably in Friedel-Crafts alkylations or acylations, phosphorylations or sulfurizations of aromatics and more preferably in phosphorylations of aromatics.

Preferred examples of phosphorylations of aromatics include the Lewis acid-catalyzed reaction of aromatics with phosphoryl halides, for example $PCl_3$, $PCl_5$, $POCl_3$ or $PBr_3$.

Examples of aromatics which can be used include those of the formula (X)

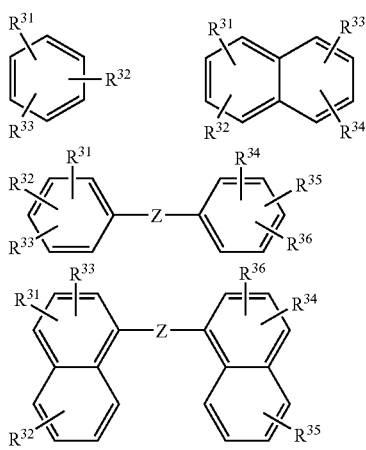

where

Z is a single bond or any desired bivalent bridge and $R^{31}$, $R^{32}$, $R^{33}$, $R^{34}$, $R^{35}$ and $R^{36}$ are each independently hydrogen, $C_1$-$C_{18}$-alkyl, or $C_2$-$C_{18}$-alkyl, $C_1$-$C_{18}$-alkyloxy, $C_1$-$C_8$-alkoxycarbonyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or functional group or two of them combine to form an unsaturated, saturated or aromatic ring which is optionally interrupted by one or more oxygen and/or sulfur atoms and/or by one or more substituted or unsubstituted imino groups, and the stated radicals in each case may be substituted by functional groups, aryl, alkyl, aryloxy, alkyloxy, halogen, heteroatoms and/or heterocycles.

Examples of functional groups therein include nitro (—$NO_2$), nitroso (—NO), carboxyl (—COOH), halogen (—F, —Cl, —Br, —I), amino (—$NH_2$, —NH($C_1$-$C_4$-alkyl), —N($C_1$-$C_4$-alkyl)$_2$), carboxamide (—$CONH_2$, —CONH ($C_1$-$C_4$-alkyl), —CON($C_1$-$C_4$-alkyl)$_2$), nitrile (—CN), thiol (—SH) or thioether functions (—S($C_1$-$C_4$-alkyl)).

The $R^{31}$, $R^{32}$, $R^{33}$, $R^{34}$, $R^{35}$ and $R^{36}$ radicals are preferably each independently hydrogen, $C_1$-$C_4$-alkyl, $C_1$-$C_4$-alkyloxy, $C_1$-$C_4$-alkyloxycarbonyl or halogen.

The $R^{31}$, $R^{32}$, $R^{33}$, $R^{34}$, $R^{35}$ and $R^{36}$ radicals are preferably each independently hydrogen, methyl, tert-butyl, ethyl, methoxy, fluorine or chlorine.

Examples of Z include a single bond, methylene, 1,2-ethylene, 1,1-ethylene, 1,1-propylene, 2,2-propylene, 1,2-phenylene, 1,4-dimethyl-2,3-phenylene, oxygen (—O—), unsubstituted or monosubstituted nitrogen (—NH— or —N($C_1$-$C_4$-alkyl)-) or sulfur (—S—).

Z is preferably a single bond, oxygen or methylene.

Particularly preferred aromatics are benzene, toluene, o-, m- or p-xylene, 2,4,6-trimethylbenzene, ethylbenzene, 1-ethyl-3-methylbenzene, 1-ethyl-4-methylbenzene, iso-propylbenzene, 1,3-di-iso-propylbenzene, tert-butylbenzene, 1,3-di-tert-butylbenzene, 1-tert-butyl-3-methylbenzene, 1-tert-butyl-3,5-dimethylbenzene, n-propylbenzene, styrene, indene, fluorene, dimethylaniline, fluorobenzene, chlorobenzene, bromobenzene, 1,2-, 1,3- or 1,4-dichlorobenzene, 1,2-, 1,3- or 1,4-difluorobenzene, 1,1'-binaphthyl, 2,2'-di($C_1$-$C_4$-alkyl)-1,1'-binaphthyl, particularly 2,2'-dimethyl-1,1'-binaphthyl, 2,2'-di($C_1$-$C_4$-alkyloxy)-1,1'-binaphthyl, particularly 2,2'-dimethoxy-1,1'-binaphthyl, 3,3'-bis($C_1$-$C_4$-alkyloxycarbonyl)-1,1'-binaphthyl, biphenyl, 3,3',5,5'-tetra($C_1$-$C_4$-alkyl)oxybiphenyl, particularly 3,3',5,5'-tetramethoxybiphenyl, 3,3',5,5'-tetra($C_1$-$C_4$-alkyl)biphenyl, particularly 3,3',5,5'-tetramethylbiphenyl, 3,3'-dimethoxy-5,5'-dimethylbiphenyl, naphthalene, 2-($C_1$-$C_4$-alkyl)naphthalene, particularly 2-methylnaphthalene, 2-($C_1$-$C_4$-alkyloxy)naphthalene, particularly 2-methoxynaphthalene or diphenylmethane.

Very particularly preferred aromatics are benzene, toluene, o-, m- or p-xylene, 2,4,6-trimethylbenzene, iso-propylbenzene, tert-butylbenzene, fluorobenzene, chlorobenzene, naphthalene and binaphthyl.

Examples of products of value which may be obtained by phosphorylations or sulfurizations of aromatics, Friedel-Crafts alkylations or acylations include ethylbenzene, acetophenone, 4-methylacetophenone, 4-methoxyacetophenone, propiophenone, benzophenone, dichlorophenylphosphine, diphenylchlorophosphine, tosyl chloride, 1,2-, 1,3- and 1,4-diethylbenzene, 1,2,3-, 1,2,4- and 1,3,5-triethylbenzene, cumene (iso-propylbenzene), tert-butylbenzene, 1,3- and 1,4-methyl-iso-propylbenzene, 9,10-dihydroanthracene, indane, cresol, 2,6-xylenol, 2-sec-butylphenol, 4-tert-butylphenol, octylphenol, nonylphenol, dodecylphenol, thymol or 2,6-di-tert-butyl-4-methylphenol.

According to the invention, the acid is removed using a nonionic, i.e. uncharged, auxiliary base. For this purpose, the above-listed auxiliary bases of the formulae (Ia) to (Ir) are particularly suitable.

In a preferred embodiment for removing Lewis acids, these are removed without predominant proportions of Brönsted acids (protic acids), i.e. the molar ratio of Brönsted acids to Lewis acids in the removed salt of the acid with the auxiliary base is not greater than 1:1, preferably not greater than 0.75:1, more preferably not greater than 0.5:1, even more preferably not greater than 0.3:1 and in particular not greater than 0.2:1.

The ppm and percentage values quoted herein refer, unless otherwise stated, to percentages by weight and ppm by weight.

EXAMPLES

Comparative Example 1

Preparation of diethoxyphenylphosphine (DEOPP)

An $N_2$-inertized 1000 ml reactor with an impeller stirrer was initially charged with 101.4 g of ethanol, 543 g of xylene and 232.7 g of triethylamine and heated to 50° C. 181.5 g of 98.6% dichlorophenylphosphine were added dropwise to this mixture over the course of 40 minutes, whereupon a colorless, easily stirrable suspension was formed. The reaction temperature was held at 50° C. by cooling. After complete addition of the dichlorophenylphosphine, the mixture was stirred for a further 60 minutes at 75-80° C. and then the precipitated hydrochloride was filtered off with suction and washed with cold xylene. The filtrate and washing xylene were united (total 859.9 g) and investigated by GC with an internal standard. The xylenic solution contained 11.8% of diethoxyphenylphosphine which corresponds to a yield of 51%.

Comparative Example 2

Preparation of diethoxyphenylphosphine (DEOPP)

An $N_2$-inertized 1000 ml reactor with an impeller stirrer was initially charged with 90.9 g of ethanol and 382.2 g of tributylamine and heated to 70° C. 162.7 g of 98.6% dichlorophenylphosphine were added dropwise to this mixture over the course of 40 minutes, whereupon a colorless solution formed which was liquid when heated and after cooling to room temperature solidified to a colorless crystalline solid. The reaction temperature was held at 50° C. by cooling. After complete addition of the dichlorophenylphosphine, the mixture was stirred for a further 60 minutes at 75 to 80° C. The 625.8 g reaction effluent, according to GC with an internal standard, contained 23.7% of diethoxyphenylphosphine which corresponds to a yield of 82.7%.

Inventive Example 1

Preparation of diethoxyphenylphosphine (DEOPP)

An $N_2$-inertized 1000 ml reactor with a pitched blade stirrer was initially charged with 188.9 g (2.3 mol) of 1-methylimidazole and 101.4 g (2.2 mol) of ethanol. Within 90 minutes, 181.5 g (1.0 mol) of 98.6% dichlorophenylphosphine were metered in. During this metering-in, the mixture was allowed to warm to 60° C., which took 6 min, and the temperature was then held by cooling during the further addition at 60° C. After the end of the addition, the mixture was still liquid, but crystallization occurred during the subsequent stirring time of 45 min. After heating to 80° C., the reaction mixture was again completely liquid. After stirring for a further hour, the stirrer was switched off. Two well-separated phases formed rapidly. After phase separation at 80° C., 199.4 g of a clear, colorless upper phase (DEOPP content by GC: 96.1%; content of 1-methylimidazole 1.7%) and 266.4 g of lower phase ("an ionic liquid") were obtained. The upper phase was distilled under reduced pressure through a 40 cm column containing 5 mm of Raschig rings. 15.8 g of a clear, colorless first fraction (GC: 76.9% DEOPP content) and 177.5 g of a colorless main fraction (GC: 99.4% DEOPP) were obtained. In the flask, only 4.3 g of the bottom product remained which according to GC contained a further 11.1% DEOPP. The DEOPP yield after distillation was 95.9%.

Inventive Example 2

Preparation of triethyl phosphite (Tep)

An $N_2$-inertized 1000 ml reactor with a pitched blade stirrer was initially charged with 425 g of 1-methylimidazole and 228.1 g of ethanol. Within 190 min, 206 g of phosphorus trichloride were added dropwise with ice cooling at an internal temperature of 23-33° C. The reaction was exothermic so that cooling was required to maintain this temperature. After about half of the quantity had been added, the reaction mixture became cloudy and two liquid phases were formed. The upper phase according to GC contained 90.0% of triethyl phosphite, the lower the hydrochloride of 1-methylimidazole. Before the phase separation, the mixture was heated to 78° C. 231.4 g of a colorless upper phase and 611.9 g of a clear lower phase were obtained. The upper phase was distilled under reduced pressure through a 30 cm glass column with a Sulzer DX packing. 177 g of triethyl phosphite with a purity of 99% were obtained. In the first and final phases, a further 28.3 g of triethyl phosphite were present. The total yield was 82.4%.

Inventive Example 3

Preparation of diethoxyphenylphosphine (DEOPP)

A 250 ml glass flask with a Teflon blade stirrer was initially charged with 85.7 g of 2-methylpyridine and 40.5 g of ethanol. 71.6 g of dichlorophenylphosphine (98.6%) were added dropwise with cooling over 25 min, so that the internal temperature remained at 20-29° C. During the addition, the hydrochloride of 2-methylpyridine precipitated. After complete addition, the mixture was heated and the hydrochloride began to melt above about 70° C. Two clear, well-defined liquid phases formed and 75.5 g of upper phase and 115.8 g of lower phase were obtained. The upper phase contained 81.6% DEOPP, so that the yield was 77.7%.

When the lower phase was neutralized with aqueous sodium hydroxide, a biphasic system was again formed. The lower phase consisted of an aqueous sodium chloride solution and the upper phase of the released 2-methylpyridine which in this way was recycled by simple liquid-liquid phase separation.

Inventive Example 4

Preparation of ethoxydiphenylphosphine (EODPP)

An $N_2$-inertized 1000 ml reactor with a pitched blade stirrer was initially charged with 141.7 g of 1-methylimidazole and 76.0 g of ethanol, and 315.8 g of chlorodiphenylphosphine were added dropwise over 30 min, which resulted in the formation of two liquid phases. The internal temperature was held below 65° C. After complete addition, the mixture was heated to 75° C., stirred for 45 min and the phases were separated, which gave 194.3 g of lower phase and 332.8 g of upper phase. The upper phase contained 96.6% of the product EODPP by GC. For further purification, the upper phase was distilled under reduced pressure through a glass column containing Raschig rings, which gave 292.5 g of 99.4% EODPP. Together with the EODPP in the first fraction, the total yield was 92.2%.

The lower phase which consisted of the liquid hydrochloride of 1-methylimidazole was admixed with 244.1 g of 25% sodium hydroxide. In order to dissolve the precipitated sodium chloride completely, a further 94.3 g of water were added until a clear solution was obtained. After addition of 450 g of n-propanol, sodium chloride again precipitated which, after further addition of 69.8 g of water, was again dissolved. Two liquid phases were obtained, and the 739.3 g upper phase contained 19.99% of water and 16.7% of 1-methylimidazole. This comprises 94.9% of the quantity of 1-methylimidazole used in the synthesis. As well as sodium chloride, the 304.2 g lower phase contained 70.6% of water and 2.2% of 1-methylimidazole. By repeated extraction with n-propanol, the content of 1-methylimidazole in the aqueous phase could be reduced to 0.4%. 1-Methylimidazole was recovered by separating the mixture of propanol and water from the upper phase of the first extraction.

Inventive Example 5

Continuous Preparation of ethoxydiphenylphosphine (EODPP)

A nitrogen-inertized reactor with a three-part pitched blade stirrer was continuously charged at 80° C. with the following feedstocks: 1) a mixture of 110.7 g of ethanol and 205.8 g of 1-methylimidazole 2) chlorodiphenylphosphine (99.4%). Stream 1) was added at 330 ml/h and stream 2) at 380 ml/h. Both feeds were below the surface. The reactor was fitted with an overflow through which the reaction mixture could continuously run out. The reactor volume below the overflow was 710 ml. The reaction temperature was held at 80° C. In order to bring the system to equilibrium, the output for the first 4 hours was discarded. The output over a duration of 1 hour was then collected and a mass balance conducted. The output consisted of two liquid phases. Over one hour, 497.2 g of upper phase and 280.8 g of lower phase were collected. 96.8% of the upper phase was EODPP. The upper phase was then distilled under reduced pressure through a column filled with Raschig rings, which gave 438.2 g of 99.74% EODPP. Together with the EODPP in the first fraction, the total yield was 96.7%.

Inventive Example 6

Continuous Preparation of ethoxydiphenylphosphine (EODPP)

A reaction mixing pump was used to continuously mix the following feed streams: 1) a mixture of 159.2 g of 1-methylimidazole and 85.4 g of ethanol 2) 372.8 g of chlorodiphenylphosphine (99.1%). From stream 1), 1257 g/h were added, from stream 2) 1928 g/h. The capacity of the mixing chamber was 3.3 ml. The head of the reaction mixing pump was held at 120° C. thermostatically. The system was brought to equilibrium over 5 min. The output was then collected for 11 min, in order to obtain a mass balance. During the mass balance run, the quantity of feedstocks was determined by weighing of the initial charges. 372.8 g of chlorodiphenylphosphine were added. The output consisted of two liquid phases. Over the 11 min, 392.2 g of upper phase and 218.3 g of lower phase were collected. 96.5% of the upper phase was EODPP, so that the gas chromatographically determined yield was 98.2%. The residence time of the reactants in the mixing chamber was 4 s. This gave a space-time yield of $0.69 \cdot 10^6$ kgm$^{-3}$h$^{-1}$.

Inventive Example 7

Continuous Preparation of ethoxydiphenylphosphine (EODPP)

A reaction mixing pump was used to continuously mix the following feed streams: 1) a mixture of 156.7 g of 1-methylimidazole and 84.1 g of ethanol 2) 370.0 g of chlorodiphenylphosphine (99.1%). From stream 1), 167.5 g/h were added, from stream 2) 257.4 g/h. The capacity of the mixing chamber was 3.3 ml. The head of the reaction mixing pump was held at 80° C. thermostatically. The system was brought to equilibrium over 60 min. The output was then collected for 87 min, in order to obtain a mass balance. During the mass balance run, the quantity of feedstocks was determined by weighing of the initial charges. 370.0 g of chlorodiphenylphosphine were added. The output consisted of two liquid phases. Over 87 min, 389.3 g of upper phase and 219.2 g of lower phase were collected. 96.8% of the upper phase was EODPP, so that the gas chromatographically determined yield was 98.5%. The residence time of the reactants in the mixing chamber was 30 s.

Inventive Example 8

Continuous Preparation of diethoxyphenylphosphine (DEOPP)

A reaction mixing pump was used to continuously mix the following feed streams: 1) a mixture of 237.1 g of 1-methylimidazole and 127.2 g of ethanol 2) 225.8 g of dichlorophenylphosphine. From stream 1), 385.6 g/h were added, from stream 2) 239.0 g/h. The capacity of the mixing chamber was 3.3 ml. The head of the reaction mixing pump was held at 80° C. thermostatically. The system was brought to equilibrium over 30 min. The output was then collected for 58 min, in order to obtain a mass balance. During the mass balance run, the quantity of feedstocks was determined by weighing of the initial charges. 225.8 g of dichlorophenylphosphine were added. The output consisted of two liquid phases. Over 58 min, 249.0 g of upper phase and 335.6 g of lower phase were collected. 95.4% of the upper phase was DEOPP, so that the gas chromatographically determined yield was 95.5%. The residence time of the reactants in the mixing chamber was 20 s.

Inventive Example 9

Continuous Preparation of diethoxyphenylphosphine (DEOPP)

A reaction mixing pump was used to continuously mix the following feed streams: 1) a mixture of 212.0 g of 1-methylimidazole and 113.7 g of ethanol 2) 201.7 g of dichlorophenylphosphine 3) recycled upper phase of the reaction output. From stream 1), 1543.5 g/h were added, from stream 2) 955.9 g/h, from stream 3) 2377 ml/h. The capacity of the mixing chamber was 3.3 ml. The head of the reaction mixing pump was held at 80° C. thermostatically. The system was brought to equilibrium over 5 min. The output was then collected for 12 min, in order to obtain a mass balance. During the mass balance run, the quantity of feedstocks was determined by weighing of the initial charges. 201.7 g of dichlorophenylphosphine were added. The output consisted of two liquid phases, which were separated in a continuously operated phase separator. A portion of the upper phase was recycled to the process. During the 12 min mass balance run, 227.0 g of upper phase and 300.6 g of lower phase were collected. 95.2% of the upper phase was DEOPP, so that the yield was 97.2%. The residence time of the reactants in the mixing chamber was 2.5 s. This gives a space-time yield of $0.36 \cdot 10^6$ kgm$^{-3}$h$^{-1}$.

Inventive Example 10

Regeneration of 1-methylimidazole hydrochloride

Inventive example 1 was repeated, except that DEOPP was prepared from 181.5 g of dichlorophenylphosphine, 101.4 g of ethanol and 189 g of 1-methylimidazole, which gave 202.2 g of upper phase having a DEOPP content of 93.9% and 265.5 g of lower phase. The upper phase additionally contained 3.7 g of 1-methylimidazole. The lower phase was mixed with 169.6 g of paraffin oil. 168 g of 50% sodium hydroxide solution were added dropwise to this mixture, which gave an easily stirrable suspension. After the addition of 12.9 g of xylene and 78.4 g of recycled xylene from a previous experiment which also contained 3.8 g of 1-methylimidazole, the water was distilled off with the aid of xylene. A total of 132.7 g of water was distilled off. When no more water was separated off, the xylene was distilled out of the reaction mixture at 30-85 mbar and 57-90° C. top temperature through a 30 cm packed column, which gave 88.4 g of distillate which contained 21.8 g of 1-methylimidazole. The distillate was reused in the next experiment as recycled xylene so that the 1-methylimidazole contained in it was always recycled to the process. After the xylene distillation, the 1-methylimidazole was distilled off at 30 mbar and 90° C. top temperature. 164.0 g of 1-methylimidazole were recovered which had a purity of 99.7%. The water content of the distilled 1-methylimidazole was 0.06%.

The distillation bottom product was then admixed with 350 g of water in order to dissolve the sodium chloride suspended in the white oil. Two phases were formed. The 475.7 g lower phase contained the sodium chloride and 0.3% (1.4 g) of 1-methylimidazole. The 161.1 g upper phase consisted of the white oil, which was likewise recycled to the process as an inert suspending auxiliary. Of the total of 192.8 g of 1-methylimidazole used (189.0 g fresh and 3.8 g in the recycled xylene), 164.0 g were recovered as pure product. A further 21.8 g were present in the xylene distilled off which was recycled to the process and therefore retained. In total, 185.8 g (96%) of the 1-methylimidazole were therefore recycled.

Inventive Example 11

51 g of acetic acid were dissolved in 120.8 g of cyclohexane. In order to remove the acid again, 69.80 g of 1-methylimidazole were added to the solution, whereupon a biphasic mixture consisting of 119.4 g of upper-phase (cyclohexane) and 122.5 g of lower phase (ionic liquid=1-methylimidazolium acetate) formed. During the addition of 1-methylimidazole, the temperature rose because of the salt formation to 40° C. The temperature during the further addition was held at 40° C. by cooling with an ice bath. After cooling, the acetic acid in the form of the formed ionic liquid which is immiscible with cyclohexane was almost completely removed from the solvent by a liquid-liquid phase separation.

Inventive Example 12

Continuous preparation of the following chelate phosphonite:

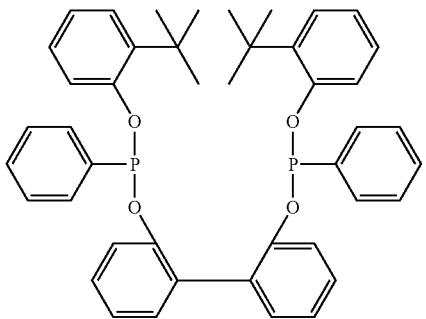

In a reaction mixing pump, the following feed streams were mixed continuously:

1) Composition: mixture of 11.9 g of 1-methylimidazole, 11.8 g of o-biphenol and 35.1 g of toluene and
2) Composition: mixture of 38.4 g of (2-tert-butylphenoxy)chlorophenylphosphine and 153.5 g of toluene.

From stream 1), 681 ml/h were metered in, and from stream 2), 2373 ml/h. The capacity of the mixing chamber was 3.3 ml. The head of the reaction mixing pump was held at 120° C. thermostatically. The system was brought to equilibrium over 3 min. The output was then collected for 7 min, in order to obtain a mass balance. The temperature of the reaction medium at the exit of the reaction mixing pump was 100° C. The output consisted of two liquid phases which were collected in a vessel and then separated. During the 7 min mass balance run, 233.9 g of upper phase and 14.0 g of lower phase were collected. The upper phase was a toluenic solution of the reaction products, and the lower phase was the hydrochloride of 1-methylimidazole which occurred as an ionic liquid above 75° C. The selectivity of the desired chelate phosphonite over the undesired monodentate phosphonites was determined with the aid of 31P NMR spectra. It was 93.8% in favor of the chelate phosphonite. The conversion was complete.

Inventive Example 13

The synthesis of the chelate phosphonite from Inventive example 12 was carried out as described under Inventive example 12. Different parameters were varied. The head of the reaction mixing pump was thermostatted in such a manner that the end temperatures of the reaction mixture at the exit of the pump specified in the table could be obtained. The results are summarized in the following table:

| Composition stream 1 | Composition stream 2 | Feed stream 1 | Feed stream 2 | Reactor exit temperature | Selectivity for chelate phosphonite relative to monodentate phosphonites |
|---|---|---|---|---|---|
| 33.3 g MIA 32.8 g BP 98.0 g Tol | 106.0 g TBCP 45.4 g Tol | 1603 ml/h | 1367 ml/h | 105.5° C. | 96.6% |
| 37.3 g MIA 36.7 g BP 109,7 g Tol | 118.7 g TBCP 50.9 g Tol | 1603 ml/h | 1367 ml/h | 90.5° C. | 97.3% |
| 41.3 g MIA 40.7 g BP 121.6 g Tol | 130.9 g TBCP 56.1 g Tol | 1603 ml/h | 1367 ml/h | 76.8° C. | 98.6% |
| 41.3 g MIA 40.7 g BP 121,6 Tol | 130.9 g TBCP 56.1 g Tol | 1603 ml/h | 1367 ml/h | 76.8° C. | 98.6% |
| 21.2 g MIA 20.9 g BP 62.5 g Tol | 71.2 g TBCP 30.5 g Tol | 1270 ml/h | 1156 ml/h | 76.3° C. | 99.3% |

MIA = 1-methylimidazole
BP = o-biphenol
Tol = toluene
TBCP = (2-tert-butylphenoxy)chlorophenylphosphine The conversion in all the variants was complete.

Inventive Example 14

Continuous preparation of the following chelate phosphonite:

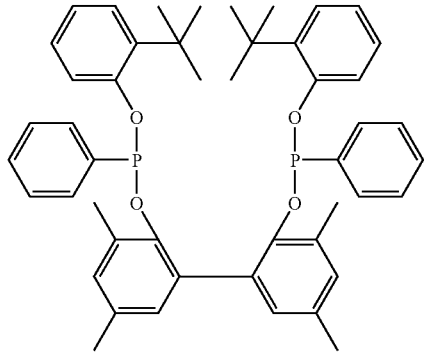

In a reaction mixing pump, the following feed streams were mixed continuously:
1) Composition: mixture of 28.0 g of 1-methylimidazole, 36.1 g of 2,2',4,4'-tetramethyl-o-biphenol and 116.4 g of toluene and
2) Composition: mixture of 88.4 g of (2-tert-butylphenoxy)chlorophenylphosphine and 37.9 g of toluene.

From stream 1), 1817 ml/h were metered in, and from stream 2), 1153 ml/h. The capacity of the mixing chamber was 3.3 ml. The system was brought to equilibrium over 2 min. The output was then collected for 5 min, in order to obtain a mass balance. The temperature of the reaction medium at the exit of the reaction mixing pump was 76.3° C. The output consisted of two liquid phases which were collected in a vessel and then separated. During the 5 min mass balance run, 264.3 g of upper phase and 40.1 g of lower phase were collected. The upper phase was a toluenic solution of the reaction products, and the lower phase was the hydrochloride of 1-methylimidazole which occurred as an ionic liquid above 75° C. The selectivity of the desired chelate phosphonite over the undesired monodentate phosphonites was determined with the aid of 31P NMR spectra. It was 95.6% in favor of the chelate phosphonite. The conversion was complete. The lower phase (ionic liquid) contained only about 300 ppm of secondary phosphorus components.

Inventive Example 15

Continuous preparation of the following chelate phosphonite:

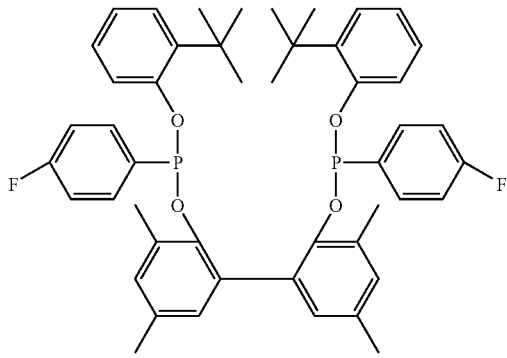

In a reaction mixing pump, the following feed streams were mixed continuously:

1) Composition: mixture of 188.9 g of 1-methylimidazole, 249.1 g of 2,2',4,4'-tetramethyl-o-biphenol and 807.4 g of toluene and
2) Composition: mixture of 664.7 g of (2-tert-butylphenoxy)-p-fluorophenylchlorophosphine and 284.9 g of toluene.

From stream 1), 1781 ml/h were metered in, and from stream 2), 1189 ml/h. The capacity of the mixing chamber was 3.3 ml. The system was brought to equilibrium over 2 min. The output was then collected for 275 min, in order to obtain a mass balance. The temperature of the reaction medium at the exit of the reaction mixing pump was 69.8° C. The output consisted of two liquid phases which were collected in a vessel and then separated. During the 275 min mass balance run, 799.6 g of upper phase and 98.9 g of lower phase were collected. The upper phase was a toluenic solution of the reaction products, and the lower phase was the hydrochloride of 1-methylimidazole which occurred as an ionic liquid above 75° C. The yield of isolated product of value was 302.9 g (93.4% of theory).

Inventive Example 16

Continuous preparation of the following chelate phosphonite:

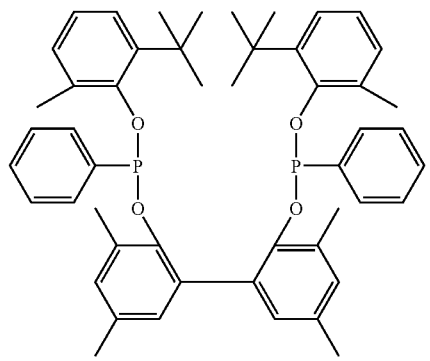

In a reaction mixing pump, the following feed streams were mixed continuously:
1) Mixture of 188.9 g of 1-methylimidazole, 249.1 g of 2,2',4,4'-tetramethyl-o-biphenol and 807.4 g of toluene and
2) Composition: mixture of 696.1 g of (2-tert-butyl-6-methylphenoxy)chlorophenylphosphine and 298.3 g of toluene.

From stream 1), 1730 ml/h were metered in, and from stream 2), 1238 ml/h. The capacity of the mixing chamber was 3.3 ml. The system was brought to equilibrium over 2 min. The output was then collected for 275 min, in order to obtain a mass balance. The temperature of the reaction medium at the exit of the reaction mixing pump was 69.5° C. The output consisted of two liquid phases which were collected in a vessel and then separated. During the 275 min mass balance run, 798.1 g of upper phase and 93.3 g of lower phase were collected. The upper phase was a toluenic solution of the reaction products, and the lower phase was the hydrochloride of 1-methylimidazole which occurred as an ionic liquid above 75° C. The yield of isolated product of value was 298.3 g (95.2% of theory).

Inventive Example 17

Continuous preparation of the following chelate phosphite:

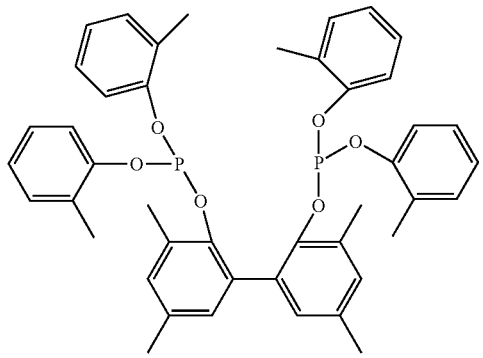

In a reaction mixing pump, the following feed streams were mixed continuously:
1) Mixture of 188.9 g of 1-methylimidazole, 249.1 g of 2,2',4,4'-tetramethyl-o-biphenol and 807.4 g of toluene and
2) Composition: mixture of 660.5 g of (di-o-cresyl)chlorophosphine and 283.1 g of toluene.

From stream 1), 1793 ml/h were metered in, and from stream 2), 1176 ml/h. The capacity of the mixing chamber was 3.3 ml. The system was brought to equilibrium over 2 min. The output was then collected for 160 min, in order to obtain a mass balance. The temperature of the reaction medium at the exit of the reaction mixing pump was 70.1° C. The output consisted of two liquid phases which were collected in a vessel and then separated. During the 160 min mass balance run, 470.8 g of upper phase and 60.8 g of lower phase were collected. The upper phase was a toluenic solution of the reaction products, and the lower phase was the hydrochloride of 1-methylimidazole which occurred as an ionic liquid above 75° C. The yield of isolated product of value was 166.6 g (93.0% of theory).

Inventive Example 18

Continuous preparation of the following chelate phosphinite:

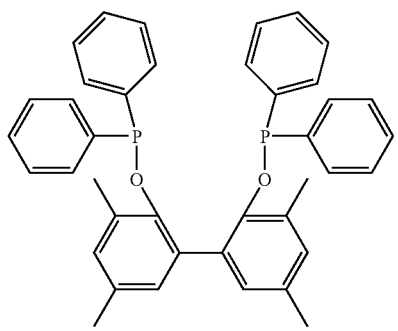

In a reaction mixing pump, the following feed streams were mixed continuously:
1) Mixture of 188.9 g of 1-methylimidazole, 249.1 g of 2,2',4,4'-tetramethyl-o-biphenol and 807.4 g of toluene and
2) Composition: mixture of 445.8 g of diphenylchlorophosphine and 191.1 g of toluene.

From stream 1), 1991 ml/h were metered in, and from stream 2), 906 ml/h. The capacity of the mixing chamber was 3.3 ml. The system was brought to equilibrium over 2 min. The output was then collected for 218 min, in order to obtain a mass balance. The temperature of the reaction medium at the exit of the reaction mixing pump was 70.1° C. The output consisted of two liquid phases which were collected in a vessel and then separated. During the 218 min mass balance run, 641.8 g of upper phase and 93 g of lower phase were collected. The upper phase was a toluenic solution of the reaction products, and the lower phase was the hydrochloride of 1-methylimidazole which occurred as an ionic liquid above 75° C. The yield of isolated product of value was 152.3 g (67.4% of theory).

Inventive Example 19

Continuous preparation of the following chelate phosphonite:

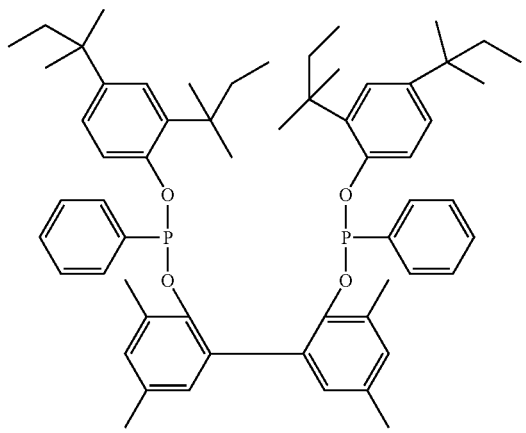

In a reaction mixing pump, the following feed streams were mixed continuously:
1) Mixture of 188.9 g of 1-methylimidazole, 249.1 g of 2,2',4,4'-tetramethyl-o-biphenol and 807.4 g of toluene and
2) Composition: mixture of 828.1 g of (2,4-diisoamylphenoxy)chlorophenylphosphine and 354.9 g of toluene.

From stream 1), 1532 ml/h were metered in, and from stream 2), 1395 ml/h. The capacity of the mixing chamber was 3.3 ml. The system was brought to equilibrium over 2 min. The output was then collected for 275 min, in order to obtain a mass balance. The temperature of the reaction medium at the exit of the reaction mixing pump was 69° C. The output consisted of two liquid phases which were collected in a vessel and then separated. During the 275 min mass balance run, 787.9 g of upper phase and 85.3 g of lower phase were collected. The upper phase was a toluenic solution of the reaction products, and the lower phase was the hydrochloride of 1-methylimidazole which occurred as an ionic liquid above 75° C. The yield of isolated product of value was 304 g (89.6% of theory).

Inventive Example 20

Continuous preparation of the following chelate phosphonite:

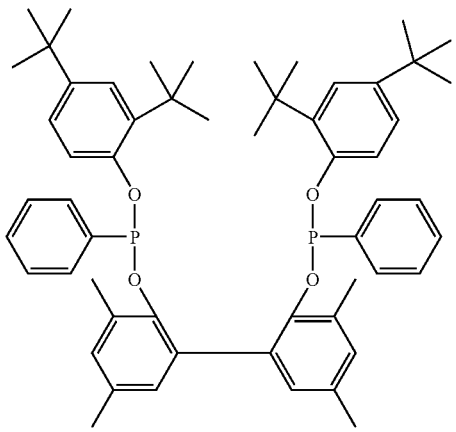

In a reaction mixing pump, the following feed streams were mixed continuously:
1) Mixture of 188.9 g of 1-methylimidazole, 249.1 g of 2,2',4,4'-tetramethyl-o-biphenol and 807.4 g of toluene and
2) Composition: mixture of 738.3 g of (2,4-di-tert-butylphenoxy)chlorophenylphosphine and 316.4 g of toluene.

From stream 1), 1664 ml/h were metered in, and from stream 2), 1308 ml/h. The capacity of the mixing chamber was 3.3 ml. The system was brought to equilibrium over 2 min. The output was then collected for 233 min, in order to obtain a mass balance. The temperature of the reaction medium at the exit of the reaction mixing pump was 75.8° C. The output consisted of two liquid phases which were collected in a vessel and then separated. During the 233 min mass balance run, 663.9 g of upper phase and 79.8 g of lower phase were collected. The upper phase was a toluenic solution of the reaction products, and the lower phase was the hydrochloride of 1-methylimidazole which occurred as an ionic liquid above 75° C. The yield of isolated product of value was 267 g (94.7% of theory).

Inventive Example 21

A 1 l flask equipped with a thermostated jacket, mechanical stirring, thermometer and reflux condenser was initially charged under an argon atmosphere with a mixture of 1.7 mol of $PCl_3$ and 0.6 mol of $AlCl_3$ (98% purity) at 73° C. 0.4 mol of fluorobenzene was then added within 30 min, while a weak argon stream was passed through the reaction flask. The reaction mixture was stirred for 3 hours and cooled to 60° C., and 0.62 mol of N-methylimidazole was added slowly within 45 min. The reaction was exothermic and mist formed. Stirring was then continued at 60° C. for a further 30 min. When the stirring was switched off, two phases separated. The lower phase was removed and the upper phase extracted twice at 60° C. with 80 ml of $PCl_3$ each time.

The lower phase and the combined $PCl_3$ extracts were distilled to obtain 55 g of p-fluorophenyldichlorophosphine in a yield of 70% of theory and a purity of 96% (determined by $^{31}P$ NMR).

Inventive Examples 22-27

Inventive example 21 was repeated, except that the ratios of fluorobenzene, $AlCl_3$, $PCl_3$ and N-methylimidazole specified in the table were used.

| Ex. | Molar ratio $AlCl_3$:fluorobenzene | Molar ratio N-methyl imidazole:$AlCl_3$ | Reaction time [h] | Yield [%] | Purity [%] |
|---|---|---|---|---|---|
| 21 | 1.5 | 1 | 3 | 70 | 96 |
| 22 | 1.5 | 1 | 6 | 65 | 96 |
| 23 | 1.5 | 1 | 3 | 80 | 91 |
| 24 | 1 | 1 | 3 | 54 | 96 |
| 25 | 1 | 0.5 | 3 | 16 | n.d. |
| 26 | 1.5 | 0.5 | 3 | 19 | n.d. |
| 27 | 2 | 1 | 3 | 79 | 73 | n.d.: not determined

In Inventive example 23, a reaction procedure similar to Inventive example 21 was selected, except that the $AlCl_3$ of a higher purity (>99%) was used.

Comparative Example 3

A 1 l flask equipped with a thermostated jacket, mechanical stirring, thermometer and reflux condenser was initially charged under an argon atmosphere with a mixture of 3.4 mol of $PCl_3$ and 1.2 mol of $AlCl_3$ (98% purity) at 73° C. 0.8 mol of fluorobenzene was then added within 30 min, while a weak argon stream was passed through the reaction flask. The reaction mixture was stirred for 3 hours and cooled to 60° C., and 1.25 mol of pyridine were added slowly within 45 min. The reaction was exothermic and mist formed. Stirring was then continued at 60° C. for a further 30 min. An irregular, large-lumped solid precipitated which could not be removed via a suction filter, but only by filtration. The residue which was filtered off was washed with petroleum ether. The filtrate and washing liquid were combined and distilled to obtain 73.3 g of p-fluorophenyldichlorophosphine in a yield of 47% of theory.

Inventive Example 28

Acetylation of pyrrolidine

A solution of 5.88 g (75.0 mmol) of acetyl chloride in 10 ml of MTBE (tert-butylmethyl ether) was added dropwise at from 10 to 15° C. to a solution of 5.33 g (75.0 mmol) of pyrrolidine in 20 ml of MTBE, and the temperature was maintained. The resulting suspension was admixed under ice-cooling with 6.76 g (82.5 mmol) of 1-methylimidazole and heated to 20° C. which converted the suspension to a liquid biphasic mixture. Stirring was continued for 1 h and the phases were separated. The upper phase was freed of solvent on a rotary evaporator which gave 6.28 g (74.1%) of N-acetylpyrrolidine. In addition to 1-methylimidazole hydrochloride, the lower phase contained further target product. After addition of water, two extractions of the upper phase with dichloromethane gave another 1.70 g (20.1%) of N-acetylpyrrolidine.

Inventive Example 29

Acetylation of 1-butanol 6.47 g (82.5 mmol) of acetyl chloride were added dropwise with stirring and ice-cooling to a solution of 5.55 g (75.0 mmol) of 1-butanol and 6.67 g (82.5 mmol) of 1-methylimidazole in such a manner that the temperature did not exceed 10° C. The reaction mixture was then heated to 75° C. which resulted in a liquid biphasic mixture. The upper phase which was removed consisted of 6.73 g (77.5%) of 1-butyl acetate which, according to GC analysis, contained about 1% of 1-methylimidazole. The lower phase solidified on cooling to 20° C.

Inventive Example 30

Acetylation of 2-butanol 6.47 g (82.5 mmol) of acetyl chloride were added dropwise with stirring and ice-cooling to a solution of 5.55 g (75.0 mmol) of 2-butanol and 12.3 g (150 mmol) of 1-methylimidazole in such a manner that the temperature did not exceed 10° C. Stirring was then continued at 0° C. for 30 min and at 20° C. for 30 min. The suspension which had formed in the meantime was then converted to a liquid biphasic mixture. The removal of the upper phase gave 7.90 g (theory: 8.68 g) of 2-butyl acetate as a colorless oil having a purity of 85% (GC).

Inventive Example 31

Acetylation of isobutanol (2-methylpropan-1-ol)

6.47 g (82.5 mmol) of acetyl chloride were added dropwise with stirring at 20° C. to a solution of 5.55 g (75.0 mmol) of isobutanol and 6.76 g (82.5 mmol) of 1-methylimidazole. The reaction mixture was stirred for a further 30 min and then heated to 75° C. The suspension which had formed in the meantime was converted to a liquid biphasic mixture. Removal of the upper phase gave 7.01 g (theory: 8.68 g) of isobutyl acetate as a colorless oil having a purity of 99% (GC).

Inventive Example 32

Acetylation of neopentyl alcohol (2,2-dimethyl-1-propanol)

6.47 g (82.5 mmol) of acetyl chloride were added dropwise with stirring at 20° C. to a solution of 6.61 g (75.0 mmol) of neopentyl alcohol (2,2-dimethyl-1-propanol) and 6.76 g (82.5 mmol) of 1-methylimidazole. The reaction mixture was stirred for a further 30 min and then heated to 75° C. The suspension which had formed in the meantime was converted to a liquid biphasic mixture. Removal of the upper phase gave 8.40 g (theory: 9.76 g) of neopentyl acetate as a colorless oil having a purity of 98% (GC).

Inventive Example 33

Benzoylation of n-butanol 11.9 g (82.5 mmol) of benzoyl chloride were added dropwise with stirring at 10° C. to a solution of 5.55 g (75.0 mmol) of 1-butanol and 6.76 g (82.5 mmol) of 1-methylimidazole. The reaction mixture was stirred for a further 30 min and then heated to 75° C. The suspension which had formed in the meantime was converted to a liquid biphasic mixture. Removal of the upper phase gave 9.90 g (theory: 13.3 g) of 1-butyl benzoate as a colorless oil having a purity of 99% (GC).

Inventive Example 34

Palmitoylation of prenol

A solution of 20.6 g (75.0 mmol) of palmitoyl chloride (C16) in 10 ml of toluene was added dropwise with stirring at from 20 to 36° C. to a solution of 6.46 g (75.0 mmol) of prenol (3-methylbut-2-en-1-ol) and 6.76 g (82.5 mmol) of 1-methylimidazole in 40 ml of toluene. The reaction mixture was stirred for a further 30 min and then heated to 80° C. The suspension which had formed in the meantime was converted to a liquid biphasic mixture. Removal of the upper phase and concentration on a rotary evaporator gave 23.6 g (theory: 24.3 g) of prenyl palmitate as a semisolid mass having a purity of 95% (GC).

Inventive Example 35

Palmitoylation of all-trans-retinol (vitamin-A alcohol, VAA)

Palmitoyl chloride (170.0 g, 0.618 mol) (C16) was added dropwise with stirring, exclusion of light and cooling within 25 min to a 29% solution of all-trans-retinol in heptane (608.5 g, 0.16 mol) and 1-methylimidazole (50.8 g, 0.62 mol). The reaction temperature rose to 15° C. The mixture was stirred at 2-5° C. for 30 min, then at room temperature for 30 min. The mixture was heated to 90° C. to form two liquid phases. The phases were separated. Apart from the solvent, the upper phase contains 0.27% of retinol and 95.2% of vitamin A palmitate (HPLC).

Inventive Example 36

Acylation with ethylhexanoyl chloride

2-Ethylhexanoyl chloride (30.0 g, 0.186 mol) is added slowly with icebath cooling and under a nitrogen atmosphere at a temperature of 10-15° C. to a solution of 4-(hydroxymethyl)-1,3-dioxolan-2-one (20.0 g, 0.169 mol) and 1-methylimidazole (MIA, 30.6 g, 0.373 mol) in methylene chloride (400 ml). The reaction mixture is stirred overnight and the solvent removed under reduced pressure. The residue is taken up twice in methyl tert-butyl ether (MTBE) and the phases in each case separated. The organic upper phase is concentrated under reduced pressure. The ester is obtained as a colorless oil containing residues of MIA. The mixture is taken up twice in toluene and the solvent removed each time under reduced pressure. 45.83 g of a yellowish oil having an MIA content of 17% (NMR) are obtained.

Inventive Example 37

Silylation of n-butanol 4.40 g (40.5 mmol) of chlorotrimethylsilane were added dropwise while stirring at 0° C. to a solution of 3.00 g (40.5 mmol) of 1-butanol and 11.1 g (135 mmol) of 1-methylimidazole. The reaction mixture was stirred at from 0 to 5° C. for a further 15 min and at 20° C. for 15 min to form a liquid biphasic mixture. Removal of the upper phase gave 5.30 g (theory: 5.93 g) of 1-trimethylsilyloxybutane as a colorless oil having a purity of 90% (GC).

Inventive Example 38

Silylation of 2-butanol 8.06 g (74.2 mmol) of chlorotrimethylsilane were added dropwise while stirring at 0° C. to a solution of 5.00 g (67.5 mmol) of 2-butanol and 6.10 g (74.2 mmol) of 1-methylimidazole. The reaction mixture was stirred at 0° C. for a further 30 min and at 80° C. for 5 min to form a liquid biphasic mixture. Removal of the upper phase gave 8.50 g (theory: 9.88 g) of 2-trimethylsilyloxybutane as a colorless, slightly cloudy oil having a purity of 96% (GC).

Inventive Example 39

Silylation of neopentyl alcohol (2,2-dimethyl-1-propanol)

6.50 g (56.7 mmol) of chlorotrimethylsilane were added dropwise while stirring at 0° C. to a solution of 5.00 g (56.7 mmol) of neopentyl alcohol (2,2-dimethyl-1-propanol) and 11.6 g (142 mmol) of 1-methylimidazole. The reaction mixture was stirred at 0° C. for a further 2 h and at 20° C. for 2.5 h. Removal of the upper phase gave 7.80 g (theory: 9.09 g) of 2,2-dimethyl-1-trimethylsilyloxypropane as a colorless oil having a purity of 96% (GC).

Inventive Example 40

Silylation of benzyl alcohol 5.50 g (51.0 mmol) of chlorotrimethylsilane were added dropwise while stirring at 0° C. to a solution of 5.00 g (46.0 mmol) of benzyl alcohol and 4.20 g (51.0 mmol) of 1-methylimidazole. The reaction mixture was stirred at 0° C. for a further 30 min and at 80° C. for 5 min to form a liquid biphasic mixture. Removal of the upper phase gave 7.30 g (theory: 8.29 g) of benzyltrimethylsilyl ether as a colorless oil having a purity of 99% (GC).

Inventive Example 41

Reaction of ethanol with silicon tetrachloride

SiCl$_4$ (50.0 g, 0.294 mol) is slowly added with icebath cooling and under an N2 atmosphere at a temperature of 10-15° C. to a solution of ethanol (54.3 g, 1.17 mol) and 1-methylimidazole (MIA, 98.9 g, 1.21 mol) in heptane (400 ml). The reaction mixture is stirred overnight and the phases are separated. 142.9 g of MIA hydrochloride are obtained as a colorless solid (theory: 141.9 g of MIA+MIA.HCl). The organic phase is cautiously concentrated, in order to keep losses of volatile product low. 48.1 g of tetraethoxysilane (theory: 61.3 g) are obtained as a slightly cloudy, colorless oil having a purity of 91.1% (GC).

Inventive Example 42

Silylation of acetylacetone 5.97 g (55.0 mmol) of chlorotrimethylsilane were added dropwise while stirring at 0° C. to a solution of 5.00 g (49.9 mmol) of acetylacetone and 4.50 g (55.0 mmol) of 1-methylimidazole. The reaction mixture was stirred at 0° C. for a further 1 h and at 80° C. for 5 min to form a liquid biphasic mixture. Removal of the upper phase gave 7.00 g (theory: 8.60 g) of 4-trimethylsilyloxypent-3-en-2-one as a bright yellow, cloudy oil having a purity of 84% (GC).

Inventive Example 43

Elimination of hydrogen bromide from 3-bromocyclohexene

A solution of 10.0 g (62.1 mmol) of 3-bromocyclohexane and 12.4 g (62.2 mmol) of N,N-dibutylpentylamine was stirred at 120° C. for 1 h, cooled to 25° C. and admixed with 30 ml of n-pentane. The mixture was heated to 30° C. to form a liquid biphasic mixture. The phases were separated and the lower phase was extracted with 30 ml of n-pentane. The pentane phases were combined and the pentane was distilled off on a rotary evaporator (20° C., 400-500 mbar). 3.50 g (theory 4.97 g) of a colorless residue remained which, according to GC chromatography, consisted predominantly of 1,3-cyclohexadiene.

We claim:

1. A process for removing acids from a reaction mixture using an auxiliary base, which comprises
    (1) conducting a reaction, wherein a reaction mixture comprising a product of value and an acid is obtained, wherein the acid is released during the reaction and/or is present during the reaction, and wherein the auxiliary base is present during the reaction or is added to the reaction mixture following the reaction,
    wherein the reaction is one of (1) a phosphorylation, (2) silylation, (3) sulfurization, (4) acylation with the exception of phosgenations, (5) elimination or (6) substitution,
    wherein the auxiliary base combines with the acid to form a salt which is liquid at temperatures at which the product of value does not significantly decompose during separating of the liquid salt from the product of value, and (a) the liquid salt of the auxiliary base with (b) the product of value or, if the product of value is entirely or substantially miscible with the salt, a solution of the product of value obtained by combining it with a solvent that reduces miscibility with the salt, forms two immiscible liquid phases, one phase containing (a) and the other phase containing (b), and
    (2) separating the two immiscible phases from each other,
    wherein the auxiliary base is selected from the group consisting of the formulae (a) to (r),

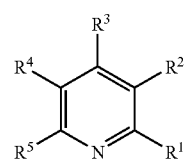

(a)

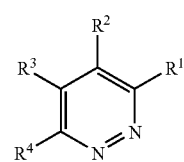

(b)

-continued (c) 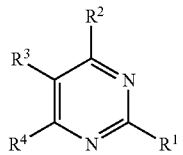

(d) 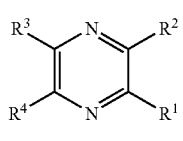

(e) 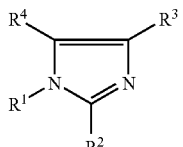

(f) 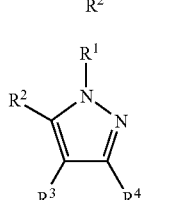

(g) 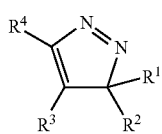

(h) 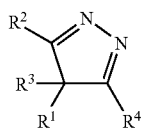

(i) 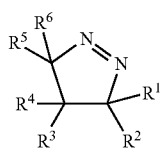

(j) 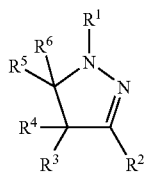

(k) 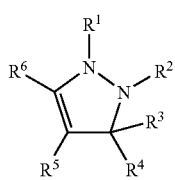

(l) 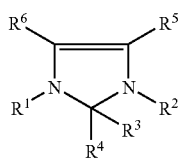

-continued (m) 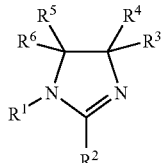

(n) 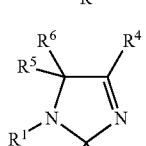

(o) 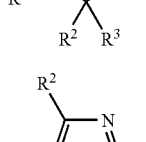

(p) 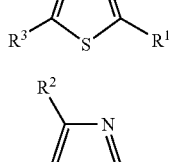

(q) 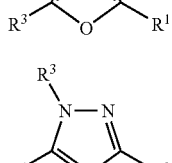

(r) 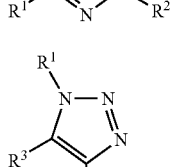

where $R^1$, $R^2$, $R^3$, $R^4$, $R^5$ and $R^6$ are each independently $C_1$-$C_{18}$-alkyl, or $C_2$-$C_{18}$-alkyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle, where the stated radicals in each case may be substituted by functional groups, aryl, alkyl, aryloxy, alkyloxy, halogen, heteroatoms and/or heterocycles, or $R^1$, $R^2$, $R^3$, $R^4$, $R^5$ and $R^6$ are each independently hydrogen, dimethylamino, diethylamino or chlorine, and wherein pyridines (a) being those where one of the radicals $R^1$ to $R^5$ is methyl, ethyl or chlorine and the rest are all hydrogen, or $R^3$ is dimethylamino and the rest are hydrogen, or $R^2$ is carboxyl or carboxamide and all the others are hydrogen, or $R^1$ and $R^2$ combined or $R^2$ and $R^3$ combined are 1,4-buta-1,3-dienylene and all the others are hydrogen.

2. The process as claimed in claim 1, wherein the auxiliary base additionally simultaneously functions as a nucleophilic catalyst.

3. The process as claimed in claim 1, wherein the salt of the auxiliary base has a melting point below 160° C.

4. The process as claimed in claim 1, wherein the salt of the auxiliary base has an $E_T(30)$ value of greater than 35.

5. The process as claimed in claim 1, wherein the auxiliary base is 1-n-butylimidazole, 1-methylimidazole, 2-methylpyridine or 2-ethylpyridine.

6. The process as claimed in claim 1, wherein the acid is hydrochloric acid, acetic acid, p-toluenesulfonic acid, methanesulfonic acid or trifluoromethanesulfonic acid.

7. The process as claimed in claim 1, wherein the molar ratio of Brönsted acids to Lewis acids in the removed salt of the acid with the auxiliary base is greater than 4:1.

8. The process as claimed in claim 1, wherein the salt of the auxiliary base is less than 20% by weight soluble in the product of value or in the solution of the product of value in the solvent.

9. The process as claimed in claim 1, wherein the acid was not released during the reaction.

10. The process as claimed in claim 1, wherein the product of value is selected from the group consisting of phosphines, phosphinic esters, phosphinous esters (phosphinites), phosphonic esters, phosphonic halides, phosphonic amides, phosphonous esters (phosphonites), phosphonous amides, phosphonous halides, phosphoric esters, phosphoric diester halides, phosphoric diester amides, phosphoric ester dihalides, phosphoric ester diamides, phosphorous esters (phosphites), phosphorous diester halides, phosphorous diester amides, phosphorous ester dihalides and phosphorous ester diamides.

11. The process as claimed in claim 10, wherein the reaction is carried out continuously at a temperature of from 60° C. to 150° C. and a residence time of 1 hour.

12. The process as claimed in claim 1, wherein the auxiliary base is in nonionic form.

13. The process as claimed in claim 1, wherein the acid is a Lewis acid.

14. The process as claimed in claim 13, wherein the reaction mixture stems from a Friedel-Crafts alkylation or acylation, phosphorylation or sulfurization of aromatics.

15. The process as claimed in claim 14, wherein the aromatic has one of the following formulae:

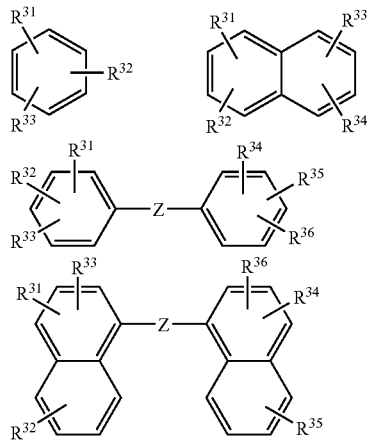

where
Z is a single bond or any desired bivalent bridge and $R^{31}$, $R^{32}$, $R^{33}$, $R^{34}$, $R^{35}$ and $R^{36}$ are each independently hydrogen, $C_1$-$C_{18}$-alkyl, or $C_2$-$C_{18}$-alkyl, $C_1$-$C_{18}$-alkyloxy, $C_1$-$C_8$-alkoxycarbonyl, $C_6$-$C_{12}$-aryl, $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or functional group or two of them combine to form an unsaturated, saturated or aromatic ring which is optionally interrupted by one or more oxygen and/or sulfur atoms and/or by one or more substituted or unsubstituted imino groups, and the stated radicals in each case may be substituted by functional groups, aryl, alkyl, aryloxy, alkyloxy, halogen, heteroatoms and/or heterocycles.

16. The process as claimed in claim 14, wherein the product of value is ethylbenzene, acetophenone, 4-methylacetophenone, 4-methoxyacetophenone, propiophenone, benzophenone, dichlorophenylphosphine, diphenylchlorophosphine, tosyl chloride, 1,2-, 1,3- or 1,4-diethylbenzene, 1,2,3-, 1,2,4- or 1,3,5-triethylbenzene, cumene (isopropylbenzene), tert-butylbenzene, 1,3- or 1,4-methylisopropylbenzene, 9,10-dihydroanthracene, indane, cresol, 2,6-xylenol, 2-sec-butylphenol, 4-tert-butylphenol, octylphenol, nonylphenol, dodecylphenol, thymol or 2,6-di-tert-butyl-4-methylphenol.

17. The process as claimed in claim 1, wherein the molar ratio of Brönsted acids to Lewis acids in the removed salt of the acid with the auxiliary base is not greater than 1:1.

18. The process as claimed in claim 1, wherein the auxiliary base does not take part in the reaction as a reactant.

19. A process for removing acids from a reaction mixture using an auxiliary base, which comprises (1) conducting a reaction, wherein a reaction mixture comprising a product of value and an acid is obtained, wherein the acid is released during the reaction and/or is present during the reaction, and wherein the auxiliary base is present during the reaction or is added to the reaction mixture following the reaction, wherein the auxiliary base combines with the acid to form a salt which is liquid at temperatures at which the product of value does not significantly decompose during separating of the liquid salt from the product of value, and (a) the liquid salt of the auxiliary base with (b) the product of value or, if the product of value is entirely or substantially miscible with the salt, a solution of the product of value obtained by combining it with a solvent that reduces miscibility with the salt, forms two immiscible liquid phases, one phase containing (a) and the other phase containing (b), and (2) separating the two immiscible phases from each other, and wherein the auxiliary base is a tertiary amine of the formula (XI)

$$NR^aR^bR^c \qquad (XI),$$

where
$R^a$, $R^b$ and $R^c$ are each independently $C_1$-$C_{18}$-alkyl, or $C_2$-$C_{18}$-alkyl, $C_6$-$C_{12}$-aryl or $C_5$-$C_{12}$-cycloalkyl, each of which may optionally be interrupted by one or more oxygen and/or sulfur atoms and/or one or more substituted or unsubstituted imino groups, or a five- to six-membered, oxygen, nitrogen and/or sulfur atom-containing heterocycle or two of them combine to form an unsaturated, saturated or aromatic ring which is optionally interrupted by one or more oxygen and/or sulfur atoms and/or one or more substituted or unsubstituted imino groups, and the stated radicals in each case may be substituted by functional groups, aryl, alkyl, aryloxy, alkyloxy, halogen, heteroatoms and/or heterocycles, with the proviso that
   at least two of the three radicals $R^a$, $R^b$ and $R^c$ are different and
   the radicals $R^a$, $R^b$ and $R^c$ together have at least 8 carbon atoms.

20. The process as claimed in claim 19, wherein $R^a$, $R^b$ and $R^c$ are selected from methyl, ethyl, n-propyl, isopropyl, n-butyl, sec-butyl, tert-butyl, n-pentyl (n-amyl), 2-pentyl (sec-amyl), 3-pentyl, 2,2-dimethylprop-1-yl (neopentyl), n-hexyl, n-heptyl, n-octyl, isooctyl, 2-ethylhexyl, 1,1-dimethylpropyl, 1,1-dimethylbutyl, benzyl, 1-phenylethyl, 2-phenylethyl, α,α-dimethylbenzyl, phenyl, tolyl, xylyl, α-naphthyl, β-naphthyl, cyclopentyl and cyclohexyl.

21. The process as claimed in claim 19, wherein the tertiary amine is selected from diiso-propylethylamine, diethyl-tert-butylamine, diisopropylbutylamine, di-n-butyl-n-pentylamine, N,N-di-n-butylcyclohexylamine and tertiary amines of pentyl isomers and triallylamine.

22. The process as claimed in claim 19, wherein the auxiliary base does not take part in the reaction as a reactant.

23. The process as claimed in claim 19, wherein the radicals $R^a$, $R^b$ and $R^c$ together have at least 10 carbon atoms.

* * * * *